US008814797B2

(12) United States Patent
Katou

(10) Patent No.: US 8,814,797 B2
(45) Date of Patent: Aug. 26, 2014

(54) ULTRASONIC DIAGNOSTIC DEVICE AND COMPUTER-READABLE MEDIUM

(75) Inventor: Yoshiki Katou, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 0 days.

(21) Appl. No.: 13/806,401

(22) PCT Filed: Mar. 9, 2011

(86) PCT No.: PCT/JP2011/055555
§ 371 (c)(1),
(2), (4) Date: Dec. 21, 2012

(87) PCT Pub. No.: WO2011/161989
PCT Pub. Date: Dec. 29, 2011

(65) Prior Publication Data
US 2013/0102904 A1    Apr. 25, 2013

(30) Foreign Application Priority Data

Jun. 22, 2010    (JP) ................................. 2010-141245

(51) Int. Cl.
*A61B 8/00*    (2006.01)
(52) U.S. Cl.
USPC ......................................... 600/437; 382/128
(58) Field of Classification Search
USPC ............................ 600/437–469; 382/128–132
See application file for complete search history.

(56) References Cited

U.S. PATENT DOCUMENTS 5,851,187 A * 12/1998 Thomas et al. ............... 600/447
6,524,254 B2 * 2/2003 Erikson .......................... 600/447
6,626,833 B2 * 9/2003 Kawagishi et al. ........... 600/443
8,485,977 B2 * 7/2013 Hirama .......................... 600/447
2009/0326377 A1 * 12/2009 Hirama .......................... 600/447
(Continued)

FOREIGN PATENT DOCUMENTS

JP    4-361740 A    12/1992
JP    5-228140 A    9/1993
(Continued)

OTHER PUBLICATIONS

Partial translation of Handbook of Ultrasonic Diagnostic Equipments; edited by Japan Electronics and Information Technology Industries; p. 94; Corona Publishing Co., Ltd.; Jan. 20, 1997.

(Continued)

*Primary Examiner* — Sanjay Cattungal
(74) *Attorney, Agent, or Firm* — Holtz Holtz Goodman & Chick PC

(57) ABSTRACT

An ultrasound diagnostic device has a control unit (18) which sequentially selects transducers (2a) for supplying drive signals while shifting a predetermined number of the transducers in a disposing direction for each output of transmitted ultrasound waves. Then, an image generation unit (14) generates image data for within a subject body for each frame on the basis of received signals which have been sequentially received by a receiving unit (13). Next, the control unit (18) performs switching between selection of m units of transducers (2a) to be consecutively positioned, and selection of m+1 units of the transducers (2a) to be consecutively positioned, for each frame. In addition, the control unit (18) generates synthesized image data acquired by synthesizing image data of at least two consecutive frames each time that image data is generated for each frame.

12 Claims, 27 Drawing Sheets

(56) References Cited

U.S. PATENT DOCUMENTS

| | | | |
|---|---|---|---|
| 2010/0036292 A1* | 2/2010 | Darlington et al. | 601/2 |
| 2010/0312114 A1* | 12/2010 | Karasawa | 600/447 |
| 2011/0319743 A1* | 12/2011 | Satoh | 600/407 |

FOREIGN PATENT DOCUMENTS

| | | |
|---|---|---|
| JP | 8-322840 A | 12/1996 |
| JP | 10-118063 A | 5/1998 |
| JP | 2000-254124 A | 9/2000 |
| JP | 2010-29374 A | 2/2010 |

OTHER PUBLICATIONS

International Search Report and Written Opinion dated Apr. 5, 2011 (in English) in counterpart International Application No. PCT/JP2011/055555.

International Preliminary Report on Patentability (IPRP) and Written Opinion dated Jan. 15, 2013 (in English) issued in parent International Application No. PCT/JP2011/055555.

* cited by examiner

FIG.20
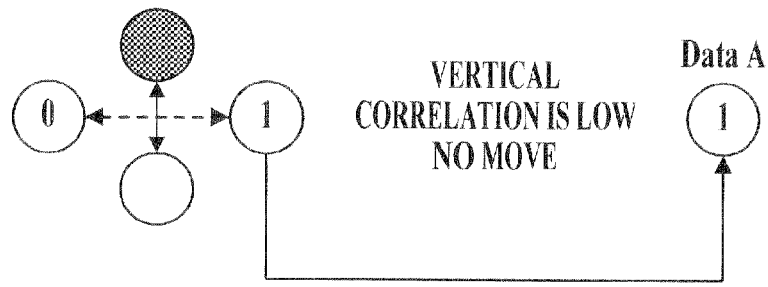
A USE Data 1 FOR Data A
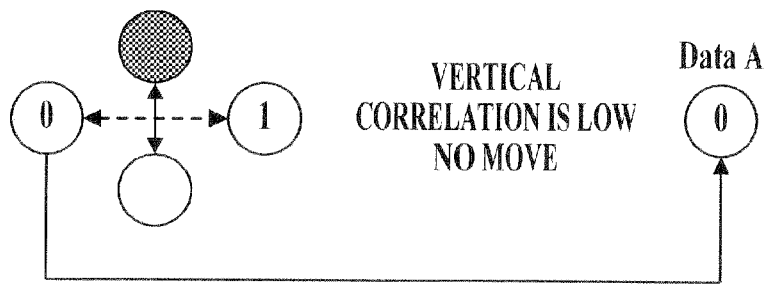
B USE Data 0 FOR Data A
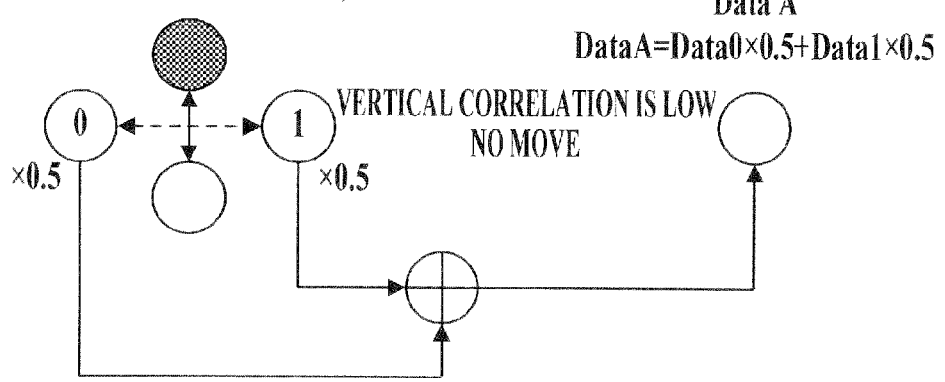
C USE AVERAGE OF Data 0, 1 FOR Data A
DataA=Data0×0.5+Data1×0.5

$(q = \frac{1}{2}p)$

ULTRASONIC DIAGNOSTIC DEVICE AND COMPUTER-READABLE MEDIUM

This application is a U.S. National Phase Application under 35 USC 371 of International Application PCT/JP2011/055555 filed Mar. 9, 2011.

TECHNICAL FIELD

The present invention relates to an ultrasound diagnostic device and a program.

BACKGROUND ART

Heretofore, there has been known an ultrasound diagnostic device, which has an oscillating probe (probe) including a large number of transducers by arraying the same one-dimensionally or two-dimensionally, selects a plurality of the transducers consecutively arranged among the large number of transducers, performs transmission/reception for an ultrasound wave, which is generated by beam forming, for a test subject such as a living body by the selected transducers, performs scanning (linear scanning) for a predetermined range thereof by repeating the transmission/reception of the ultrasound wave while shifting the transducers to be selected, and creates an ultrasound image, which is in accordance with the B mode and for each frame, based on data obtained as a result of this scanning.

Here, as shown in FIG. 26, a minimum value of an interval q between targets (focus points) T to be specified by ultrasound beams created by the beam forming is equal to an arrangement interval p between transducers $1002a$. That is to say, the minimum value (azimuth resolution) of the recognizable interval q between the targets T depends on the arrangement interval p between the transducers $1002a$. Therefore, in the ultrasound diagnostic device as mentioned above, the arrangement interval between the transducers just needs to be reduced in order to enhance the azimuth resolution; however, there are physical limitations thereon.

Accordingly, in the conventional ultrasound diagnostic device, there is one configured as follows. After the transmission/reception for the ultrasound wave is performed a predetermined number of times while shifting the transducers to be selected, a transducer array itself is moved by a predetermined distance in an array direction, the transmission/reception for the ultrasound wave is performed a predetermined number of times in a similar way, and such a transmission/reception operation is executed a plurality of times in one frame, then received signals obtained as a result are synthesized with one another, and image data for one frame is created (for example, Patent Literature 1).

Moreover, as shown in FIG. 27, it is also known to change the number of transducers $1002a$, which are to be selected for each transmission/reception of the ultrasound wave, alternately to odd numbers/even numbers, and the scanning is performed while shifting the targets T (for example, Non-Patent Literature 1).

PRIOR ART LITERATURES

Patent Literatures

Patent Literature 1: Japanese Patent Laid-Open Publication No. 2010-29374

Non-Patent Literature 1: "Handbook of Ultrasonic Diagnostic Equipments (original is in Japanese)", edited by Japan Electronics and Information Technology Industries Association, p. 94, Corona Publishing Co., Ltd.

SUMMARY OF THE INVENTION

Problems to be Solved by the Invention

However, though in the ultrasound diagnostic device described in the foregoing patent literature, the azimuth resolution can be enhanced since the interval between the targets can be reduced while the arrangement interval between the transducers is being left as it is, a frame rate is lowered since the number of transmission/reception times of the ultrasound wave in one frame is increased, and an accurate diagnosis is inhibited from being performed. Moreover, complicated mechanism and device for moving the transducer array are required, and cost is increased.

Moreover, also in the technology shown in FIG. 27, though the azimuth resolution can be enhanced since the interval q between the targets T becomes a half of the arrangement interval p between the transducers $1002a$, the frame rate is still lowered since the number of transmission/reception times of the ultrasound wave in one frame is increased.

It is an object of the present invention to provide an ultrasound diagnostic device and a program, which are capable of enhancing the azimuth resolution while suppressing the frame rate from being lowered.

Means for Solving the Problems

In order to achieve the foregoing object, according to an aspect of the invention, an ultrasound diagnostic device is provided which comprises:

an ultrasound probe which includes n (n>1) pieces of transducers being arranged in parallel, the transducers outputting transmitted ultrasound waves toward a test body by a drive signal, and outputting received signals by receiving reflected ultrasound waves from the test body;

a transmitter unit which supplies the drive signal to selected transducers among the n pieces thereof;

a receiver unit which receives received signals to be outputted from the selected transducers;

a control unit which sequentially selects the transducers, the transducers being to be supplied with the drive signal, while shifting the transducers by a predetermined number in an array direction every time when each of the transmitted ultrasound waves is outputted; and an image processing unit which creates image data of an inside of the test body for each frame based on the received signals sequentially received by the receiver unit, wherein, while making switch for each frame, the control unit executes selection of m (m<n) pieces of the transducers arranged consecutively and selection of m+1 pieces of the transducers arranged consecutively, and every time when the image data of each frame is created, at least creates synthetic image data obtained by synthesizing image data of two consecutive frames with each other.

According to a further aspect of the invention, the ultrasound diagnostic device further comprises:

a storage unit which at least stores image data of a range from a latest frame among the two consecutive frames to a third latest frame, wherein the control unit creates pixel data of a pixel in the synthetic image data, the pixel data corresponding to a changed portion of a pixel between image data of the latest frame and image data of the third latest frame, based on pixel data in image data of a second latest frame, the pixel data corresponding to a pixel adjacent to the pixel.

According to a further aspect of the invention, the control unit sets the pixel data of the pixel in the synthetic image data, the pixel data corresponding to the changed portion of the pixel, to one obtained by interpolation from the pixel data in the image data of the second latest frame, the pixel data individually corresponding to pixels adjacent to both sides of the pixel in an azimuth direction.

According to a further aspect of the invention, the control unit sets the pixel data of the pixel in the synthetic image data, the pixel data corresponding to the changed portion of the pixel, to the same one as the pixel data in the image data of the second latest frame, the pixel data corresponding to a pixel adjacent to either side of the pixel in an azimuth direction.

According to a further aspect of the invention, the control unit sets pixel data of a pixel in the synthetic image data, the pixel data corresponding to a portion where there is no change of a pixel between the image data of the latest frame and the image data of the third frame, to pixel data of a pixel in the image data of the latest frame, the pixel data corresponding to the pixel.

According to a further aspect of the invention, the control unit determines whether or not two pixels adjacent to each other in the azimuth direction in the image data of the second latest frame, the two pixels serving as determination subject pixels, satisfy a predetermined correlation condition, and when the correlation condition is satisfied as a result of the determination, sets pixel data of a pixel to be arranged between two pixels in the synthetic image, the pixels corresponding to the determination subject pixels, to one created based on pixel data related to the determination subject pixels.

According to a further aspect of the invention, the control unit determines, as the correlation condition, whether or not a brightness difference between the determination subject pixels is a predetermined threshold value or less.

According to another aspect of the invention, a program is provided for allowing a computer, the computer being provided in an ultrasound diagnostic device including an ultrasound probe which includes n (n>1) pieces of transducers being arranged in parallel, the transducers outputting transmitted ultrasound waves toward a test body by a drive signal, and outputting received signals by receiving reflected ultrasound waves from the test body, to realize: a transmission function to supply the drive signal to selected transducers among the n pieces thereof;

a reception function to receive received signals to be outputted from the selected transducers;

a control function to sequentially select the transducers, the transducers being to be supplied with the drive signal, while shifting the transducers by a predetermined number in an array direction every time when each of the transmitted ultrasound waves is outputted, and, while making switch for each frame, to execute selection of m (m<n) pieces of the transducers arranged consecutively and selection of m+1 pieces of the transducers arranged consecutively; and an image processing function to create image data of an inside of the test body for each frame based on the received signals sequentially received by the receiver unit, and, every time when the image data of each frame is created, to at least create synthetic image data obtained by synthesizing image data of two consecutive frames with each other.

Effects of the Invention

In accordance with the present invention, the azimuth resolution can be enhanced while suppressing the frame rate from being lowered.

BRIEF DESCRIPTION OF THE DRAWINGS

FIG. 20 is a view explaining creation of pixels in the synthetic image.

MODE FOR CARRYING OUT THE INVENTION

Figure 1:
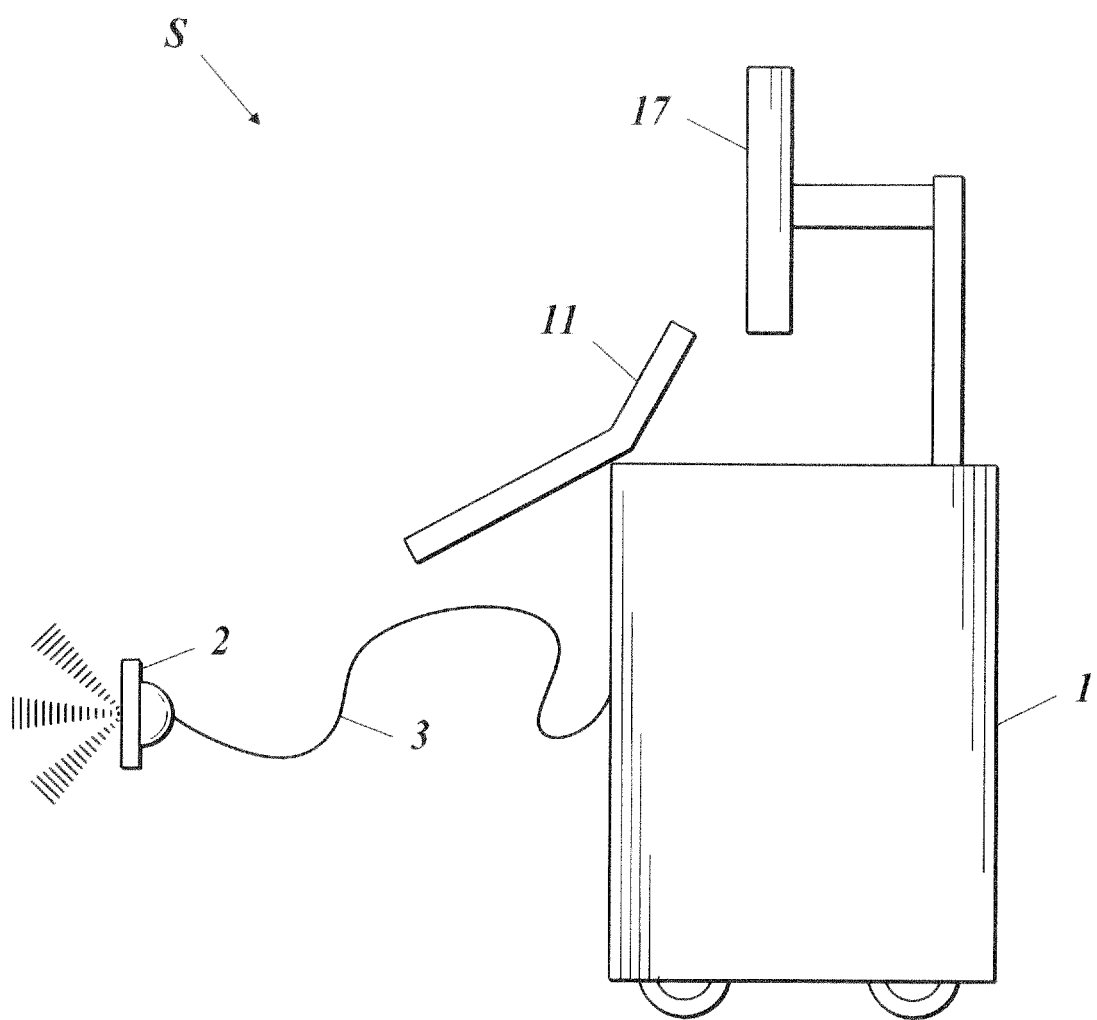
FIG. 1 is a view showing an exterior appearance configuration of an ultrasound diagnostic device in an embodiment of the present invention.

A description is made below of ultrasound diagnostic devices according to embodiments of the present invention with reference to the drawings. However, the scope of the invention is not limited to illustrated examples. Note that, in the following description, the same reference numerals are assigned to those having the same functions and configurations, and a description thereof is omitted.

First Embodiment

Figure 2:
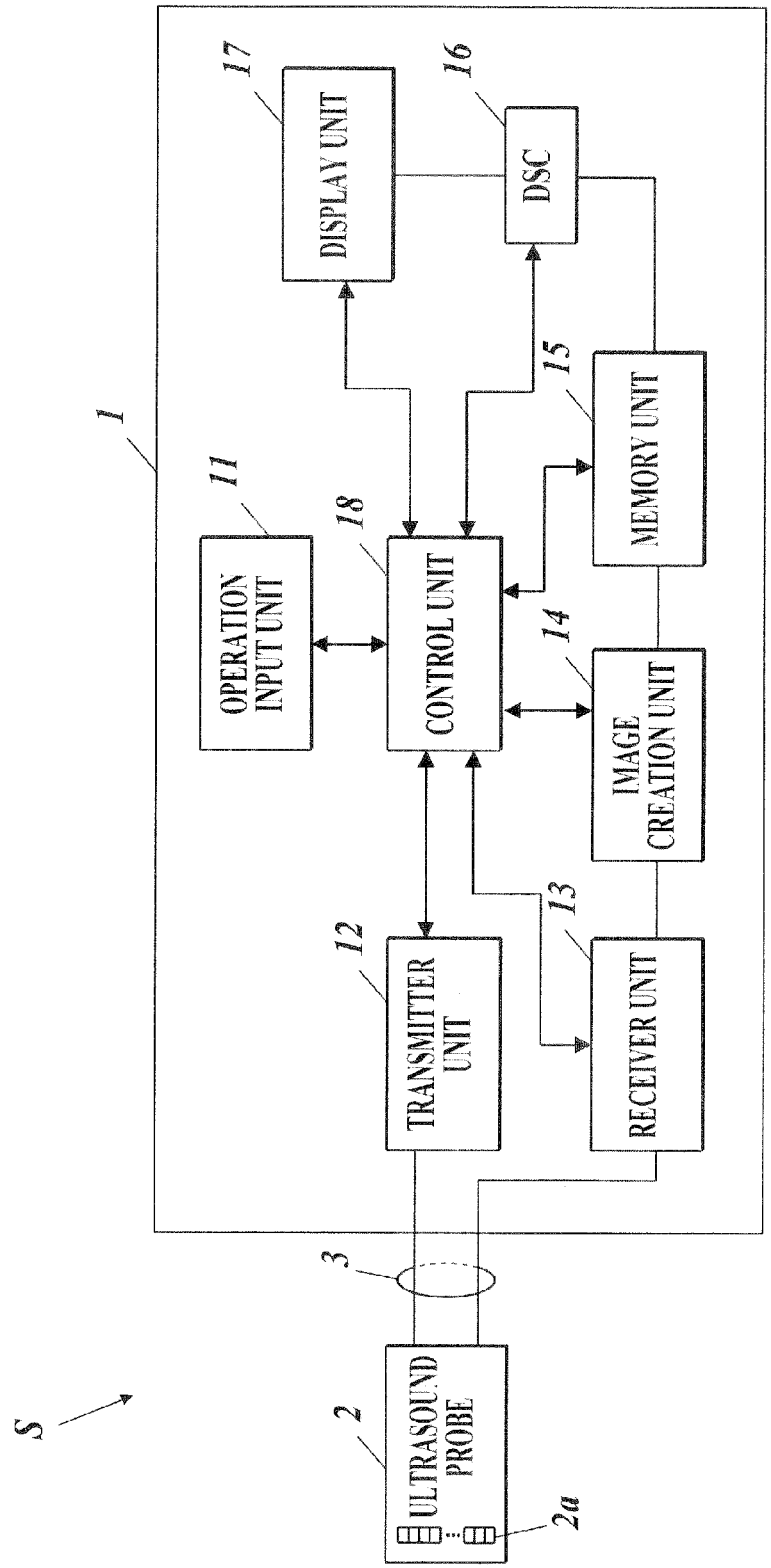
FIG. 2 is a block diagram showing a schematic configuration of the ultrasound diagnostic device.

As shown in FIG. 1 and FIG. 2, an ultrasound diagnostic device S according to a first embodiment of the present invention is composed by including: an ultrasound probe 2, which transmits an ultrasound wave (transmitted ultrasound wave) to a test subject (not shown) such as a living body, and in addition, receives an ultrasound reflected wave (reflected ultrasound wave: echo) reflected on this test subject; and an ultrasound diagnostic device body 1, which is connected to the ultrasound probe 2 through a cable 3, allows the ultrasound probe 2 to transmit the transmitted ultrasound wave to the test subject by transmitting a drive signal as an electric signal to the ultrasound probe 2, and in addition, images an internal state of the test subject as an ultrasound image based on a received signal as an electric signal created by the ultrasound probe 2 in response to the reflected ultrasound wave from an inside of the test subject, which is received in the ultrasound probe 2.

Figure 3:
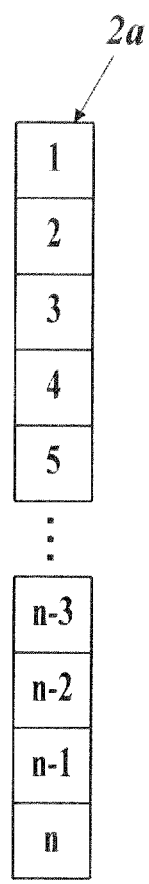
FIG. 3 is a view explaining an arrangement configuration of transducers provided in an ultrasound probe.

The ultrasound probe 2 includes transducers 2a composed of piezoelectric elements, and as shown in FIG. 3, a plurality of the transducers 2a are arrayed in a one-dimensional array form in an azimuth direction (scanning direction or vertical direction). In this embodiment, the ultrasound probe 2, which includes n pieces (for example, 128 pieces) of the transducers 2a, is used. Note that the transducers 2a may be those arrayed in a two-dimensional array form. Moreover, the number of transducers 2a may be set arbitrarily as long as the number is plural. Moreover, in this embodiment, with regard to the ultrasound probe 2, one that conducts a linear scanning mode is applied; however, those which conduct a sector scanning mode and a convex scanning mode may be applied.

For example, as shown in FIG. 2, the ultrasound diagnostic device 1 is composed by including: an operation input unit 11; a transmitter unit 12; a receiver unit 13; an image creation unit 14; a memory unit 15; a DSC (Digital Scan Converter) 16; a display unit 17; and a control unit 18.

For example, the operation input unit 11 includes a variety of switches, buttons, a track ball, a mouse, a keyboard and the like, which are for performing input of a command to instruct a start of a diagnosis and of data such as personal information of the test subject, and the like, and outputs an operation signal to the control unit 18.

The transmitter unit 12 is a circuit, which, in accordance with control of the control unit 18, supplies the drive signal as the electric signal to the ultrasound probe 2 through the cable 3, and allows the ultrasound probe 2 to generate the ultrasound wave. Moreover, for example, the transmitter unit 12 includes a clock generation circuit, a delay circuit, and a pulse generation circuit. The clock generation circuit is a circuit, which generates a clock signal that decides transmission timing and transmission frequency of the drive signal. The delay circuit is a circuit for setting a delay time for each individual route corresponding to each of the transducers 2a with regard to the transmission timing of the drive signal, delaying the transmission of the drive signal by the set delay time, and focusing transmitted beams composed of such transmitted ultrasound waves thus delayed. The pulse generation circuit is a circuit for generating a pulse signal as the drive signal in a predetermined cycle.

The receiver unit 13 is a circuit, which receives the received signal as the electric signal from the ultrasound probe 2 through the cable 3 in accordance with control of the control unit 18. For example, the receiver unit 13 includes an amplifier, an A/D converter circuit, and a phasing/adding circuit. The amplifier is a circuit for amplifying the received signal by a predetermined amplification factor, which is set in advance, for each individual route corresponding to each of the transducers 2a. The A/D converter circuit is a circuit for performing A/D conversion for the received signal thus amplified. The phasing/adding circuit is a circuit for giving a delay time to the received signal, which is subjected to the A/D conversion, for each individual route corresponding to each of the transducers 2a to phase a time phase thereof, adding (phasing/adding) such received signals to one another to create sound ray data.

The image creation unit 14 implements logarithmic amplification, envelope detection processing and the like for the sound ray data coming from the receiver unit 13, and creates B-mode image data. The B-mode image data created in such a manner is transmitted to the memory unit 15.

For example, the memory unit 15 is composed of a semiconductor memory such as a DRAM (Dynamic Random Access Memory), and stores the B-mode image frame, which is transmitted from the image creation unit 14, in a unit of frame. That is to say, the memory unit 15 can store the B-mode image frame as frame image data. As will be described later, the memory unit 15 includes frame buffers for an amount of two frames correspondingly to each of frames for which odd-number scanning is executed and of frames for which even-number scanning is executed, and can store the frame image data in the frame buffers. The frame image data stored in the memory unit 15 is made capable of being read out by the control unit 18. Moreover, as will be described later, the memory unit 15 is used as a work area in the event of creating synthetic image data by the control unit 18. Then, the created synthetic image data is transmitted to the DSC 16 in accordance with control of the control unit 18.

The DSC 16 converts the synthetic image data, which is created by the control unit 18, into an image signal in accordance with a scanning mode of a television signal, and outputs the image signal to the display unit 17.

The display unit 17 is a display device such as an LCD (Liquid Crystal Display), a CRT (Cathode-Ray Tube) display, an organic EL (Electronic Luminescence) display, and a plasma display. The display unit 17 performs display of an image on a display screen in accordance with the image signal outputted from the DSC 16. Note that a printing device such as a printer may be applied in place of the display device.

For example, the control unit 18 is composed by including a CPU (Central Processing Unit), a ROM (Read Only Memory), and a RAM (Random Access Memory), reads out a variety of processing programs such as a system program stored in the ROM, expands the processing programs in the RAM, and controls operations of the respective units of the ultrasound diagnostic device S in accordance with the expanded programs.

The ROM is composed of a nonvolatile memory such as a semiconductor, and the like, and stores the system program corresponding to the ultrasound diagnostic device S, the various programs of processing such as pulse transmission processing, pulse reception processing, and image data synthesis processing, which are executable on the system program concerned and will be described later, a variety of data, and the like. These programs are stored in a form of a program code readable by a computer, and the CPU sequentially executes operations which conform to the program code concerned. The RAM forms a work area that temporarily stores the variety of programs to be executed by the CPU and data related to these programs.

Figure 4:
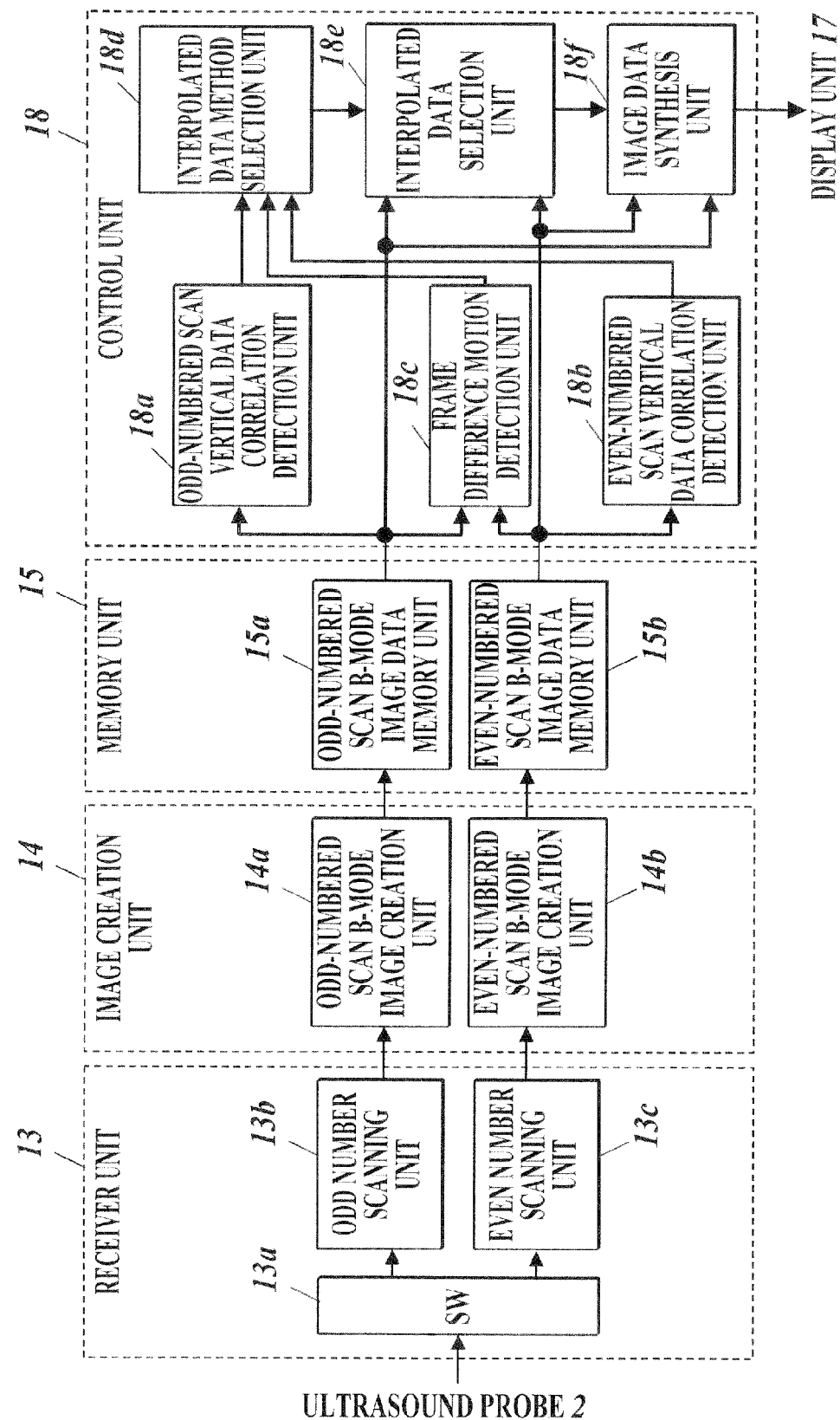
FIG. 4 is a functional block diagram for explaining a creation procedure of image data according to the embodiment of the present invention.

Next, while referring to FIG. 4, a description is made of functions in the respective units for creating the synthetic image data based on the received signal coming from the ultrasound probe 2 by the ultrasound diagnostic device S configured as described above.

As shown in FIG. 4, the receiver unit 13 includes a switch 13a, an odd number scanning unit 13b, and an even number scanning unit 13c.

The switch 13a is one that switches a route of the received signal by control of the control unit 18. When the receiver unit 13 receives the received signal from the ultrasound probe 2, the switch 13a is switched for either of an odd number frame or an even number frame, which will be described later, depending on whether the received signal belongs to the odd number frame or the even number frame, the received signal is sent to the odd number scanning unit 13b or the even number scanning unit 13c, the creation of the sound ray data is performed, and the created sound ray data is outputted to the image creation unit 14. As will be described later, the odd number frames and the even number frames are alternately executed for each of the frames, and accordingly, the switch 13a switches alternately for each of the frames. The image creation unit 14 includes an odd-numbered scan B-mode image creation unit 14a and an even-numbered scan B-mode image creation unit 14b, and in each thereof, processes the sound ray data outputted from the receiver unit 13, and creates the B-mode image data. That is to say, based on the sound ray data outputted from the odd number scanning unit 13b, the odd-numbered scan B-mode image creation unit 14a creates the B-mode image data, and based on the sound ray data outputted from the even number scanning unit 13c, the even numbered scan B-mode image creation unit 14b creates the B-mode image data. Then, the B-mode image data created in the odd-numbered scan B-mode image creation unit 14a and the even-numbered scan B-mode image creation unit 14b are outputted to the memory unit 15.

The memory unit 15 includes an odd-numbered scan B-mode image data memory unit 15a and an even-numbered scan B-mode image data memory unit 15b, and in each thereof, stores the B-mode image data outputted from the image creation unit 14. That is to say, the odd-numbered scan B-mode image data memory unit 15a stores the B-mode image data created in the odd-numbered scan B-mode image creation unit 14a, and the even-numbered scan B-mode image data memory unit 15b stores the B-mode image data created in the even-numbered scan B-mode image creation unit 14b.

The odd-numbered scan B-mode image data memory unit 15a can at least store frame image data of an amount of two frames, and frame image data created in a latest odd number frame and frame image data created in a second latest odd number frame are stored therein. Note that, for the purpose of enhancing accuracy of motion determination by the frame difference motion detection unit 18c to be described later, frame image data created in third latest odd number frame or more can be further stored therein.

Moreover, the even-numbered scan B-mode image data memory unit 15b can at least store frame image data of an amount of two frames, and frame image data created in a latest even number frame and frame image data created in a second latest even number frame are stored therein. Note that, for the purpose of enhancing the accuracy of the motion determination by the frame difference motion detection unit 18c to be described later, frame image data created in third latest even number frame or more can be further stored therein.

The control unit 18 includes an odd-numbered scan vertical data correlation detection unit 18a, an even-numbered scan vertical data correlation detection unit 18b, a frame difference motion detection unit 18c, an interpolated data method selection unit 18d, an interpolated data selection unit 18e, and an image data synthesis unit 18f. Configurations of these respective units are those to be realized by execution of software programs by the control unit 18. Note that it is also possible to realize the configurations of these respective units by hardware.

In the case where the latest frame is an even number frame, the odd-numbered scan vertical data correlation detection unit 18a reads out frame image data, which is created in an odd number frame immediately before the latest even number frame, from the odd-numbered scan B-mode image data memory unit 15a, extracts two pixels (determination subject pixels) adjacent to each other in the scanning direction, and determines a correlation therebetween. Specifically, the odd-numbered scan vertical data correlation detection unit 18a performs determination as to whether or not the correlation is strong based on whether or not a brightness difference between the extracted two pixels is less than a predetermined threshold value. For example, in the case where brightness is represented by 256 steps, this threshold value is set at "20"; however, it is possible to set the threshold value at any value as long as the threshold value is within a range where it can be determined that the correlation is strong. Then, the odd-numbered scan vertical data correlation detection unit 18a sends a determination result of the correlation to the interpolated data method selection unit 18d. This determination of the correlation is performed for all pixels in the frame image data created in the odd number frame immediately before the latest even number frame.

In the case where the latest frame is an odd number frame, the even-numbered scan vertical data correlation detection unit 18b reads out frame image data, which is created in an even number frame immediately before the latest odd number frame, from the even-numbered scan B-mode image data memory unit 15b, extracts two pixels (determination subject pixels) adjacent to each other in the scanning direction, and determines a correlation therebetween. A specific determination method is similar to that of the odd-numbered scan vertical data correlation detection unit 18a, and accordingly, a description thereof is omitted. Then, the even-numbered scan vertical data correlation detection unit 18b sends a determination result of the correlation to the interpolated data method selection unit 18d. This determination of the correlation is performed for all pixels in the frame image data created in the even number frame immediately before the latest odd number frame. The frame difference motion detection unit 18c reads out the frame image data of the latest frame and the frame image data of the third latest frame, extracts pixels on the same coordinate, compares brightnesses thereof with each other, and performs the motion determination. Specifically, for example, in the case where the latest frame is an odd number frame, the frame image data created in the latest odd number frame and the frame image data created in the second latest odd number frame (that is, the third latest frame) are read out from the odd-numbered scan B-mode image data memory unit 15a, and pixels on the same coordinate are extracted. Then, it is determined whether or not a brightness difference between these pixels is less than a predetermined threshold value, whereby determination as to whether or not the pixel concerned has moved. For example, this threshold value is set at "15"; however, it is possible to set the threshold value at any value as long as the threshold value is within a range where it can be determined that the pixel has moved. Then, the frame difference motion detection unit 18c sends a result of the motion determination to the interpolated data method selection unit 18d. This motion determination is performed for all pixels in the read out frame image data.

In this embodiment, the motion determination is performed in such a manner as described above; however, for the purpose of enhancing the accuracy of the motion determination, there may be adopted such a configuration that both of the brightness difference of the pixels between the latest frame and the third latest frame and of a brightness difference of pixels between the third latest frame and the fifth latest frame are determined, and that the motion determination is performed based on results of this determination. Moreover, there may be adopted such a configuration that a brightness difference of pixels between frames before the fifth latest frame is further determined, and that a result of this determination is used for the motion determination.

The interpolated data method selection unit 18*d* receives the individual determination results from the odd-numbered scan vertical data correlation detection unit 18*a*, the even-numbered scan vertical data correlation detection unit 18*b* and the frame difference motion detection unit 18*c*, selects a creation method of the respective pixels in the event of creating the synthetic image data to be described later, and sends information of such selection to the interpolated data selection unit. In the first embodiment, the selectable creation method of the pixels is a method of extracting a pixel, which corresponds to a pixel that becomes adjacent to a pixel (pixel of interest) serving as a subject in the event where the synthetic image data is created, from the frame image data of the second latest frame, and of obtaining interpolated pixel data, or the like.

The interpolated data selection unit 18*e* receives such selection information coming from the interpolated data method selection unit 18*d*, reads out necessary frame image data from the odd-numbered scan B-mode image data memory unit 15*a* and the even-numbered scan B-mode image data memory unit 15*b*, extracts pixel data of a pixel, which is necessary to create the pixel of interest, from the read out frame image data, and creates the pixel data of the pixel of interest. The interpolated data selection unit 18*e* sends the created image data to the image data synthesis unit 18*f*.

The image data synthesis unit 18*f* reads out the frame image data of the latest frame and the frame image data of the second latest frame from the odd-numbered scan B-mode image data memory unit 15*a* and the even-numbered scan B-mode image data memory unit 15*b*, synthesizes the respective readout frame image data with each other, and creates the synthetic image data. Moreover, when the pixel data sent from the interpolated data selection unit 18*e* is present, the image data synthesis unit 18*f* writes the pixel data concerned to the synthetic image data. Then, the synthetic image data created in such a manner is outputted to the display unit 17 through the DSC 16.

Figure 5:
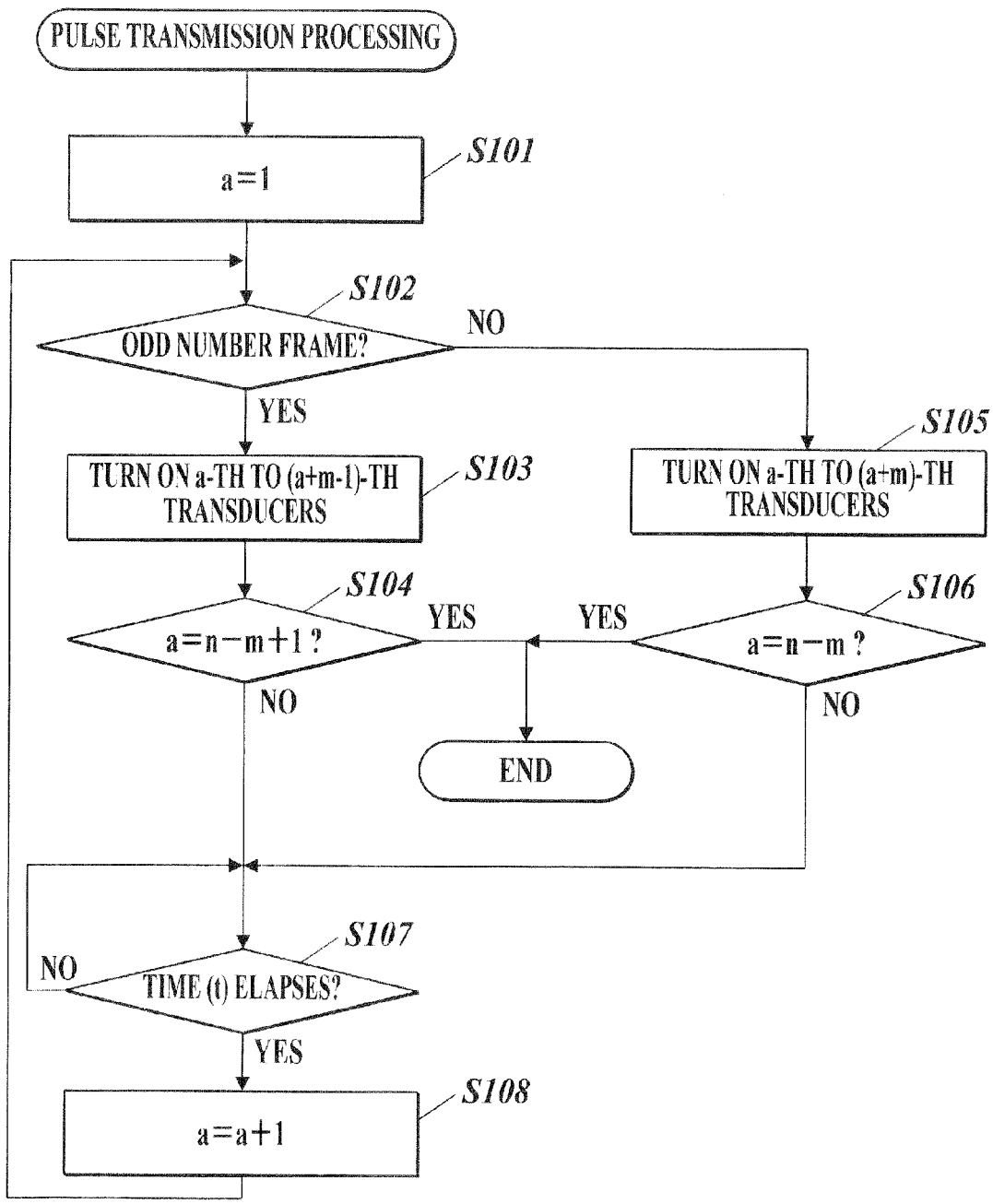
FIG. 5 is a flowchart explaining pulse transmission processing.

Next, while referring to FIG. 5, a description is made of the pulse transmission processing to be executed in the ultrasound diagnostic device S configured in such a manner as described above. This pulse transmission processing is processing to be executed when scanning in one frame is started. Note that FIG. 5 is a flowchart showing a case where, in a case where a constant m is an odd number, a frame (odd number frame), in which m pieces of the transducers 2*a* arranged consecutively in the scanning direction are driven to perform the scanning, and a frame (even number frame), in which m+1 pieces of the transducer 2*a* are driven to perform the scanning, are alternately performed. However, a configuration may be adopted, in which, the constant m is defined to be an even number, and a frame (even number frame), in which m pieces of the transducers 2*a* are driven to perform the scanning, and a frame (odd number frame), in which m+1 pieces of the transducer 2*a* are driven to perform the scanning, are alternately performed.

First, the control unit 18 sets 1 to a variable a indicating the number of output times of the transmitted ultrasound wave (Step S101), and determines whether or not a frame at this time is an odd number frame (Step S102). Here, the odd number frame is a frame, in which predetermined odd-number pieces (m pieces in the example shown in FIG. 5) of the transducers 2*a* are driven to perform the scanning, and the even number frame is a frame, in which the transducers 2*a* of which number (m+1 pieces in the example shown in FIG. 5) is larger (or smaller) by one than that of the transducers 2*a* to be driven in the odd number frame are driven to perform the scanning.

In the case where it is determined that the frame at this time is an odd number frame (Step S102: Y), the control unit 18 turns on a route from the transducer 2*a* arranged at an [a]-th position corresponding to a variable a to the transducer 2*a* arranged at an [a+m−1]-th position, and conducts the route concerned to the pulse generation circuit of the transmitter unit 12 (Step S103). That is to say, the control unit 18 makes conduction between the pulse generation circuit and m pieces (m is an odd number) of the transducers 2*a* arranged consecutively in the scanning direction, the transducers 2*a* including the transducer 2*a* located at the position corresponding to the variable a. A specific description is made with reference to FIG. 3. For example, when the number of output times is third, and the number of transducers 2*a* to be driven for each single output of the transmitted ultrasound wave is defined to be (m=3) pieces, the third to fifth transducers 2*a* and the pulse generation circuit are conducted to each other. Then, the respective transducers 2*a* output such transmitted ultrasound waves at predetermined pieces of timing thereof in response to the output of the pulse signal by the pulse generation circuit, whereby the transmitted beams are formed. Note that the constant m can be set arbitrarily as long as the constant m is smaller than the number (n pieces) of the transducers 2*a* provided in the ultrasound probe 2.

Next, the control unit 18 determines whether or not the variable a is equal to [n−m+1] (Step S104). That is to say, the control unit 18 determines whether or not the transmitted beam is the last transmitted beam in one frame, which is outputted in such a manner that m pieces of the transducers 2*a* including the transducer 2*a* arrayed in the n-th order are driven. When the control unit 18 determines that the transmitted beam concerned is a transmitted beam outputted last time in one frame (Step S104: Y), the control unit 18 ends this processing, and meanwhile, when the control unit 18 does not determine that the transmitted beam concerned is the transmitted beam outputted last time in one frame (Step S104: N), the control unit 18 shifts to processing of Step S107.

Moreover, when the control unit 18 does not determine that the frame at this time is an odd number frame in Step S102, that is, when the frame at this time is an even number frame (Step S102: N), the control unit 18 turns on a rout from the transducer 2*a* arranged at the [a]-th position corresponding to the variable a to the transducer 2*a* arranged at an [a+m]-th position, and conducts the route concerned to the pulse generation circuit of the transmitter unit 12 (Step S105). That is to say, the control unit 18 makes conduction between the pulse generation circuit and [m+1] pieces of the transducers 2*a* arranged consecutively in the scanning direction, the transducers 2*a* including the transducer 2*a* located at the position corresponding to the variable a. Then, the respective transducers 2*a* output the transmitted ultrasound waves at predetermined pieces of timing thereof in response to the output of the pulse signal by the pulse generation circuit, whereby the transmitted beams are formed.

Next, the control unit 18 determines whether or not the variable a is equal to [n−m] (Step S106). That is to say, the control unit 18 determines whether or not the transmitted beam concerned is the last transmitted beam in one frame, which is outputted in such a manner that [m+1] pieces of the transducers 2*a* including the transducer 2*a* arrayed in the n-th order are driven. When the control unit 18 determines that the transmitted beam concerned is a transmitted beam outputted last time in one frame (Step S106: Y), the control unit 18 ends this processing, and meanwhile, when the control unit 18 does not determine that the transmitted beam concerned is the transmitted beam outputted last time in one frame (Step S106: N), the control unit 18 shifts to processing of Step S107.

In Step S107, the control unit 18 waits for elapse of a predetermined time (t) (Step S107), and shifts to processing of Step S108. This time (t) is set at a cycle in which the pulse signal is generated by the pulse generation circuit of the transmitter unit 12. Then, the control unit 18 adds one to the variable a (Step S108), and shifts to the processing of Step S102.

Figure 6:
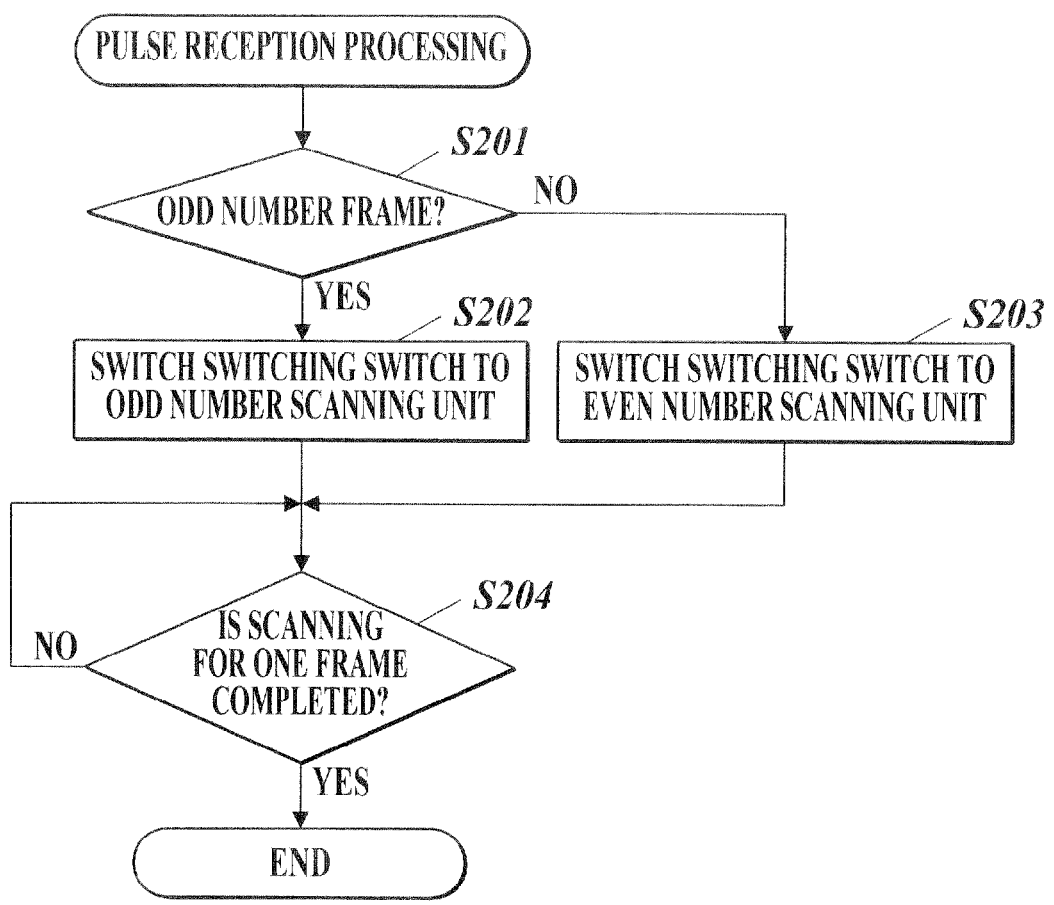
FIG. 6 is a flowchart explaining pulse reception processing.

Next, while referring to FIG. 6, a description is made of the pulse reception processing. This pulse reception processing is processing to be executed when the scanning in one frame is started.

First, the control unit 18 determines whether or not the frame at this time is an odd number frame (Step S201). When the control unit 18 determines that the frame at this time is an odd number frame (Step S201: Y), the control unit 18 switches the switch 13*a* of the receiver unit 13 so that the received signal coming from the ultrasound probe 2 can be inputted to the odd number scanning unit 13*b* (Step S202). Meanwhile, when the control unit 18 does not determine that the frame at this time is an odd number frame, that is, determines that the frame at this time is an even number frame (Step S201: N), the control unit 18 switches the switch 13*a* of the receiver unit 13 so that the received signal coming from the ultrasound probe 2 can be inputted to the even number scanning unit 13*c* (Step S203). Then, the control unit 18 waits until scanning for one frame is completed (Step S204), and ends this processing. That is to say, when the input of the received signal that is based on the last output of the transmitted beam in one frame is completed, this processing is ended.

Figure 7:
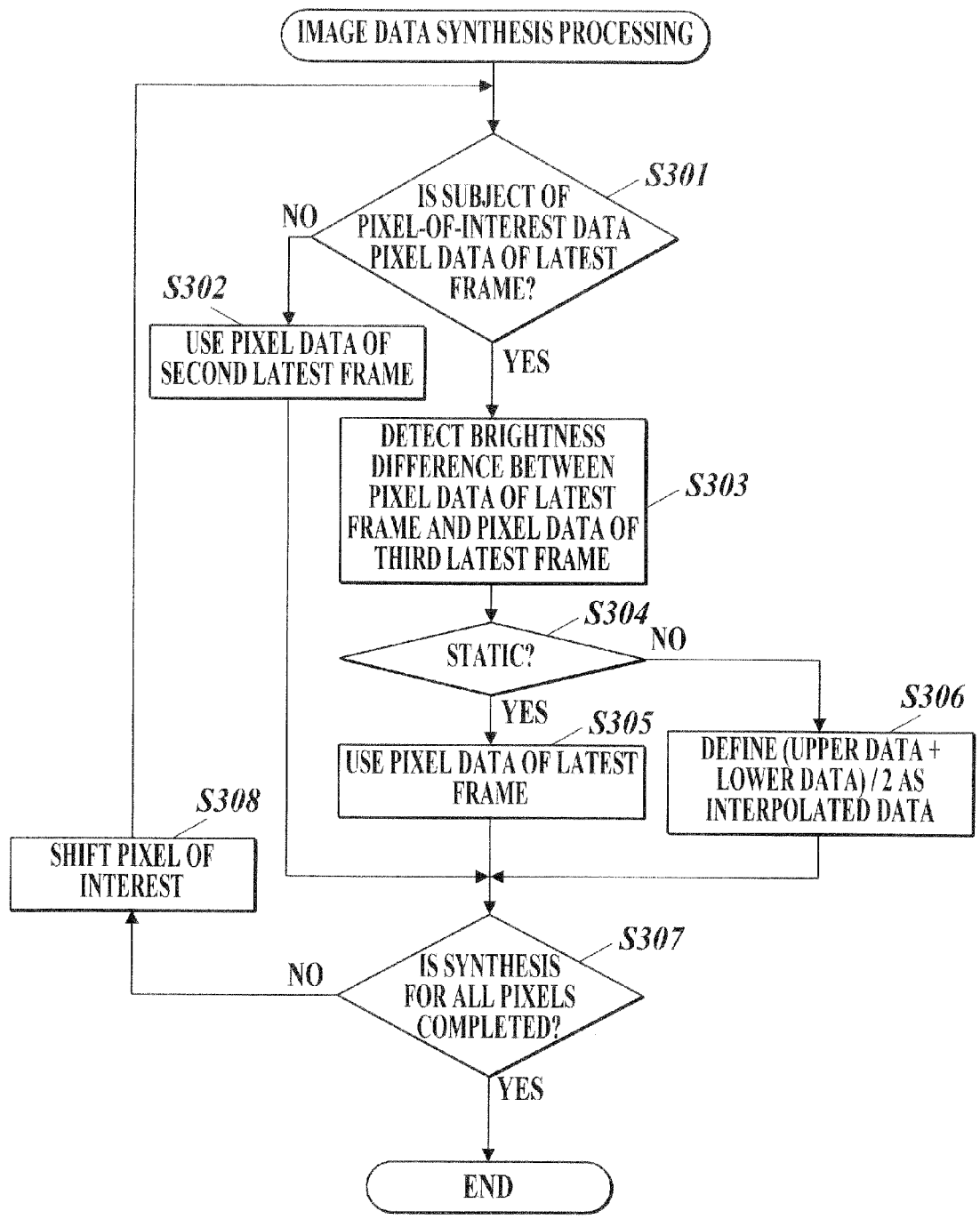
FIG. 7 is a flowchart explaining image data synthesis processing in a first embodiment.

Next, while referring to FIG. 7, a description is made of the image data synthesis processing according to the first embodiment of the present invention. This image data synthesis processing is processing to be executed when the frame image data of the latest frame is stored in the memory unit 15. Here, the latest frame refers to a latest frame between two consecutive frames which serve as bases for creating the synthetic image data, and in usual, there applies a latest frame in the frames in which the frame image data is stored in the memory unit 15 at the point of time of performing the image data synthesis processing; however, the latest frame is not necessarily limited to this. For example, in the event of creating the synthetic image data, frame image data obtained after the frames which serve as the bases for creating the synthetic image data are obtained may be already stored in the memory unit 15. Note that, in the first embodiment, the odd-numbered scan vertical data correlation detection unit 18*a* and the even-numbered scan vertical data correlation detection unit 18*b* do not function, and only by the frame difference motion detection unit 18*c*, the selection of the creation method of the pixels by the interpolated data method selection unit 18*d* is performed.

First, the control unit 18 refers to the work area in the memory unit 15, which is for creating the synthetic image data, and determines whether or not the subject of the pixel data of the pixel of interest, which is the pixel of the determination subject, is pixel data in the frame image data of the latest frame (Step S301).

When the control unit 18 does not determine that the subject of the pixel data of the pixel of interest is the pixel data in the frame image data of the latest frame (Step S301: N), the control unit 18 uses, as the pixel data of the pixel of interest, the pixel data in the frame image data of the second latest frame (even number frame immediately before the latest frame, for example, in the case where the latest frame is an odd number frame) (Step S302). That is to say, by a function of the image data synthesis unit 18*f*, the control unit 18 reads out the frame image data of the second latest frame from the memory unit 15, extracts pixel data of a pixel that coincides with the pixel of interest on the coordinate, and writes the extracted pixel data into the work area of the memory 15.

Meanwhile, when the control unit 18 determines that the subject of the pixel data of the pixel of interest is the pixel data in the frame image data of the latest frame (Step S301: Y), then by a function of the frame difference motion detection unit 18*c*, the control unit 18 detects a brightness difference between the pixel data in the frame image data of the latest frame and the pixel data in the frame image data of the third latest frame (odd number frame immediately before the latest frame, for example, in the case where the latest frame is an odd number frame), and performs the motion determination (Step S303).

Then, the control unit 18 determines whether or not the pixel of interest does not move, that is, is in a static state as a result of the motion determination (Step S304). When the control unit 18 determines that the pixel of interest is in the static state (Step S304: Y), the control unit 18 uses the pixel data in the frame image data of the latest frame (Step S305). That is to say, by the function of the image data synthesis unit 18*f*, the control unit 18 reads out the frame image data of the latest frame from the memory unit 15, extracts the pixel data of the pixel that coincides with the pixel of interest on the coordinate, and writes the extracted pixel data into the work area of the memory 15. Note that, in Step S305, in place of using the image data of the latest frame, the image data of the third latest frame may be used, or an average value of the image data of the latest frame and the image data of the third latest frame, or the like may be used.

Meanwhile, when the control unit 18 does not determine in Step S304 that the pixel of interest is in the static state, that is, when the pixel moves (Step S304: N), then by functions of the interpolated data method selection unit 18*d* and the interpolated data selection unit 18*e*, the control unit 18 extracts pixel data of pixels, which correspond to pixels adjacent to the pixel of interest in the vertical direction (scanning direction), from the frame image data of the second latest frame, and writes interpolated data, which is created by obtaining an average of the respective pixel data, into the work area of the memory unit 15 (Step S306).

Then, the control unit 18 determines whether or not the synthesis is completed for all the pixels (Step S307), and ends this processing when the control unit 18 concerned determines that the synthesis is completed (Step S307: Y). Meanwhile, when the control unit 18 does not determine that the synthesis is not completed (Step S307: N), the control unit 18 shifts the pixel of interest to an unprocessed pixel (Step S308), and thereafter, shifts to the processing of Step S301.

Next, a description is made of an aspect of the scanning and a creation process of the synthetic image data in the ultrasound diagnostic device S configured in such a manner as mentioned above.

Figure 8:
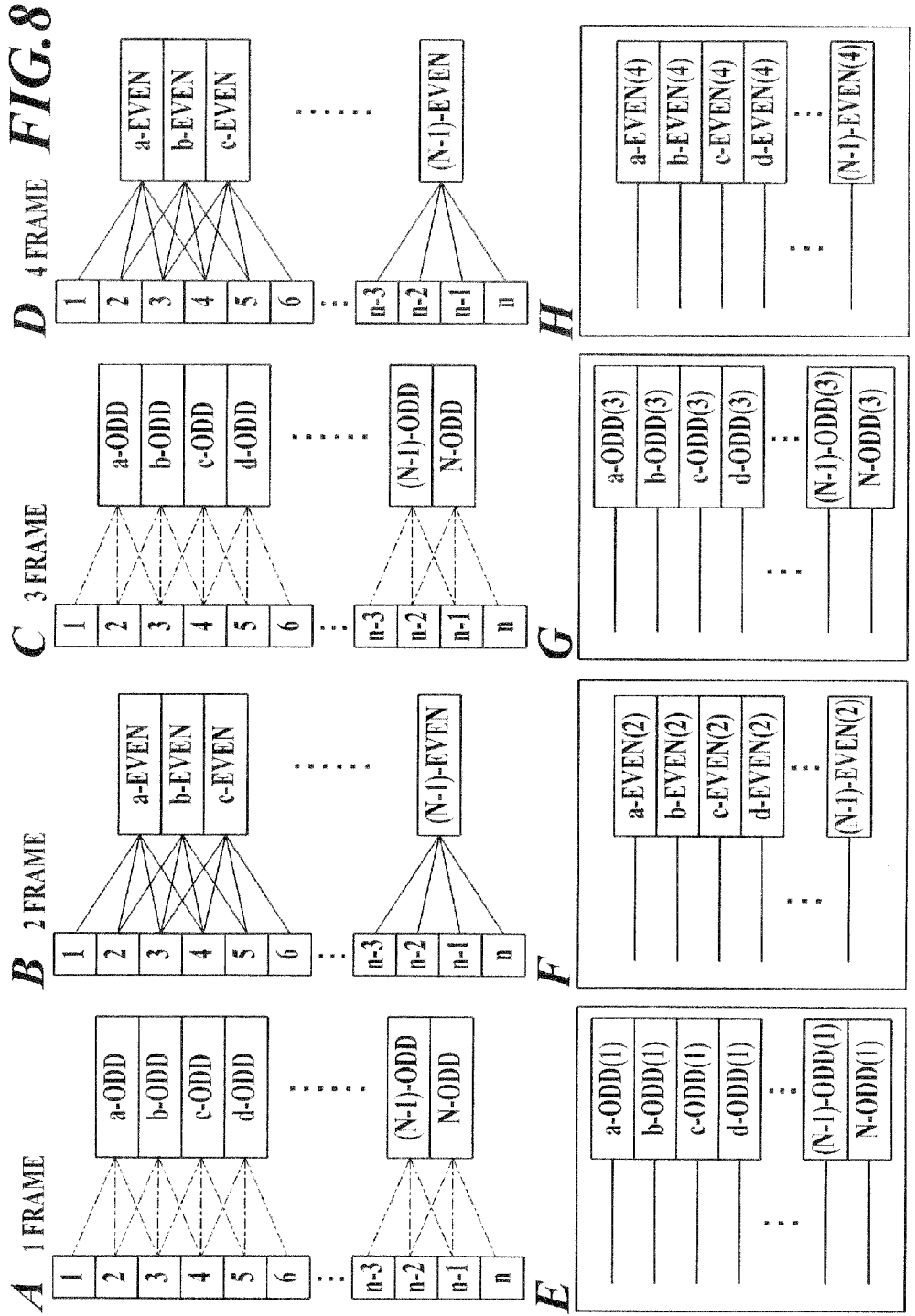
FIG. 8 is a view explaining scanning operations.

In each of the embodiments of the present invention, as shown in FIG. 8A, when the first frame as an odd number frame is started, first to third three transducers 2a are first driven, and transmitted ultrasound waves are outputted to "a-ODD" taken as a target. Subsequently, second to fourth transducers 2a are driven, and transmitted ultrasound waves are outputted to "b-ODD" taken as a target. Below in a similar way, the scanning is performed while shifting the transducers 2a, which are to be driven, until output of transmitted ultrasound waves by drive of the (n−2)-th to n-th transducers 2a is performed. Frame image data composed of the respective sound ray data, which are "a-ODD (1)" to "N-ODD (1)" to be created by this scanning, become as shown in FIG. 8E.

Then, as shown in FIG. 8B, when a second frame as an even number frame is started, first to fourth four transducers 2a are first driven, and transmitted ultrasound waves are outputted to "a-EVEN" taken as a target. Note that a position of this target is located at an intermediate between "a-ODD" and "b-ODD". Subsequently, second to fifth transducers 2a are driven, and transmitted ultrasound waves are outputted to "b-EVEN" taken as a target. Below in a similar way, the scanning is performed while shifting the transducers 2a, which are to be driven until output of transmitted ultrasound waves by drive of the (n−3) to n-th transducers 2a is performed. Frame image data composed of the respective sound ray data, which are "a-EVEN (2)" to "(N−1)-EVEN (2)" to be created by this scanning, become as shown in FIG. 8F.

Subsequently, in a third frame as an odd number frame, as shown in FIG. 8C, the scanning is performed in a similar way to the first frame, and frame image data as shown in FIG. 8G is created.

Then, in a fourth frame as an even number frame, as shown in FIG. 8D, the scanning is performed in a similar way to the second frame, and frame image data as shown in FIG. 8H is created.

Below, also in a fifth frame and after, frame image data are sequentially created in a similar procedure.

Figure 9:
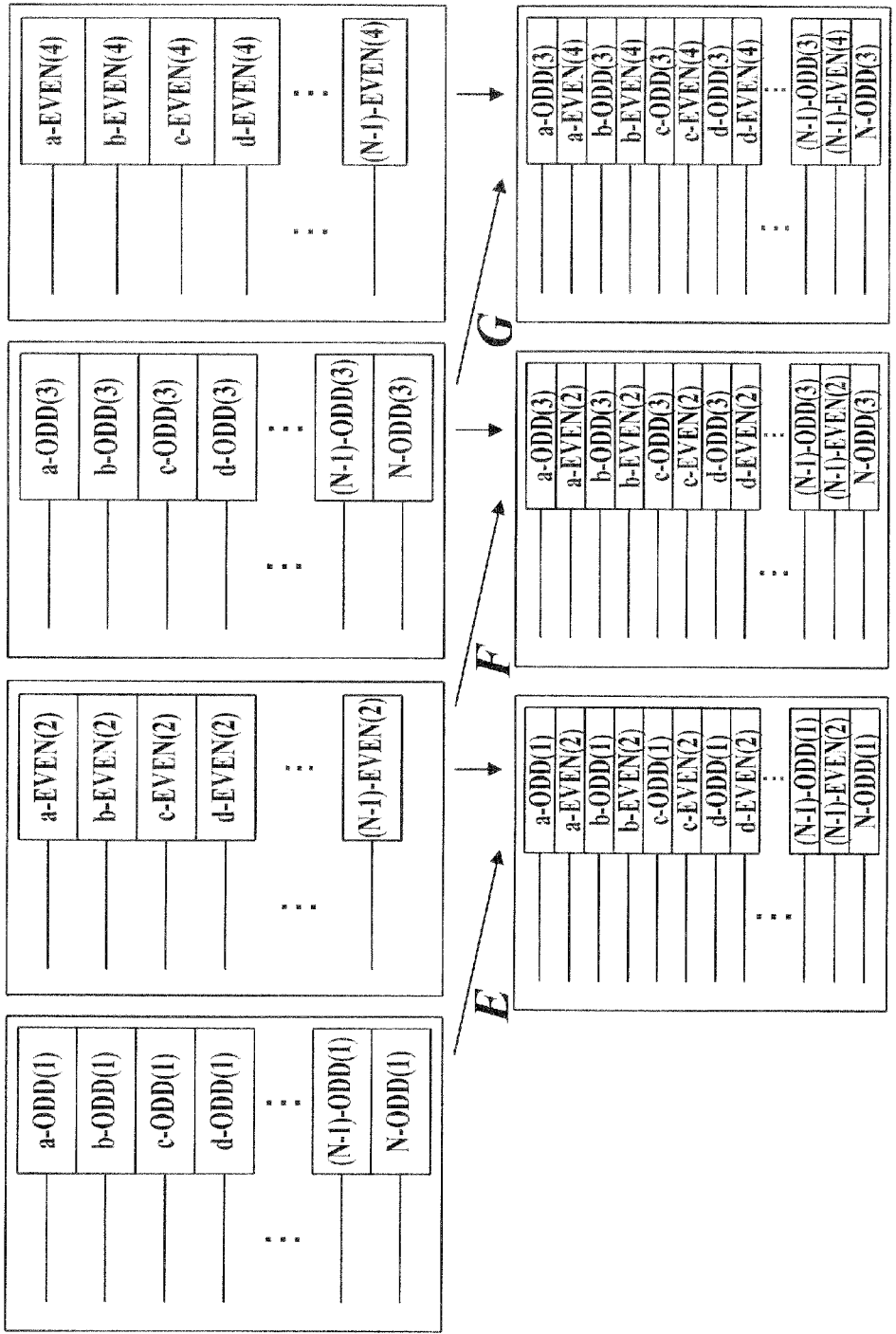
FIG. 9 is a view explaining creation of a synthetic image.

The frame image data created in such a manner as described above are synthesized with one another in an aspect as shown in FIG. 9, and the synthetic image data is created. That is to say, first, when the frame image data of the second frame is created, the respective sound ray data in the frame image data of the first frame shown in FIG. 9A and the respective sound ray data in the frame image data of the second frame shown in FIG. 9B are alternately superimposed on each other, and synthetic image data as shown in FIG. 9E is created. Then, when the frame image data of the third frame is created, the respective sound ray data in the frame image data of the second frame shown in FIG. 9B and the respective sound ray data in the frame image data of the third frame shown in FIG. 9C are alternately superimposed on each other, and synthetic image data as shown in FIG. 9F is created. Then, when the frame image data of the fourth frame is created, the respective sound ray data in the frame image data of the third frame shown in FIG. 9C and the respective sound ray data in the frame image data of the fourth frame shown ion FIG. 9D are alternately superimposed on each other, and synthetic image data as shown in FIG. 9G is created.

A pitch of the targets of the synthetic image data created in such a manner as described above becomes a half of a pitch of the targets in the respective frame image data, and the azimuth resolution is enhanced. Moreover, the synthetic image data is created every time when the frame image data of each of the frames is created, and accordingly, the lowering of the frame rate is suppressed.

Next, a description is specifically made of the synthetic image data to be created in such a manner as mentioned above.

FIG. 10A and FIG. 10B show a position of an actual object, and FIG. 10B shows a state after elapse of one frame from FIG. 10A. Moreover, FIG. 10C and FIG. 10D individually show frame image data created in the states of FIG. 10A and FIG. 10B, respectively, and FIG. 10E shows synthetic image data as a result of synthesizing the frame image data shown in FIG. 10C and FIG. 10D with each other.

Moreover, FIG. 11A and FIG. 11B show positions of an actual object, and FIG. 11B shows a state after elapse of one frame from FIG. 11A. Moreover, FIG. 11C and FIG. 11D individually show frame image data created in the states of FIG. 11A and FIG. 11B, respectively, and FIG. 11E shows synthetic image data as a result of synthesizing the frame image data shown in FIG. 11C and FIG. 11D with each other.

Figure 10:
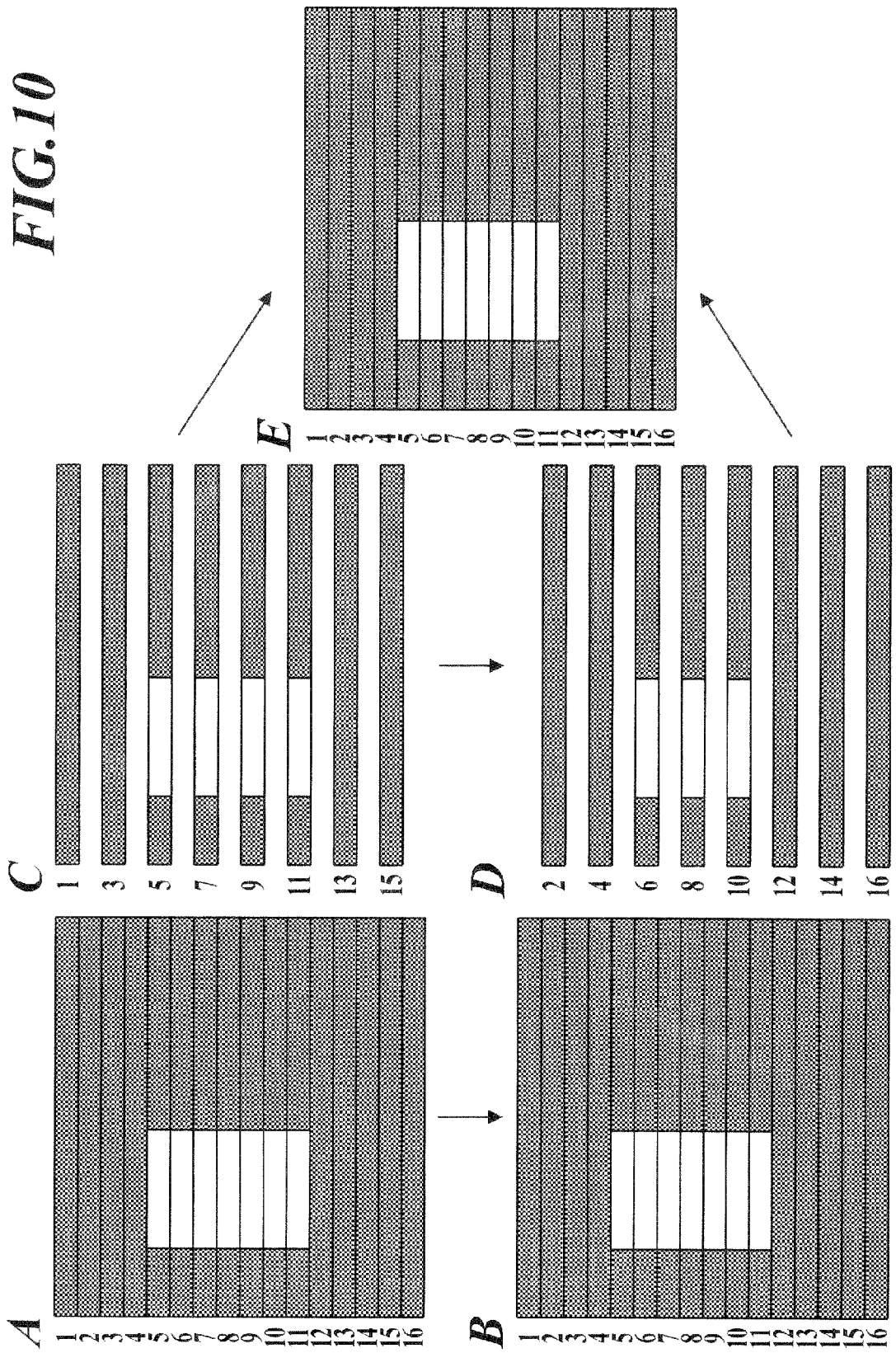
FIG. 10 is a view explaining the synthetic image.

In the example shown in FIG. 10, as shown in FIG. 10A and FIG. 10B, the object is in a static state during one frame. Therefore, when the frame image data obtained in the respective frames are synthesized with each other to create the synthetic image data, then as shown in FIG. 10E, synthetic image data that that represents substantially the same shape as that of the actual object can be obtained.

Figure 11:
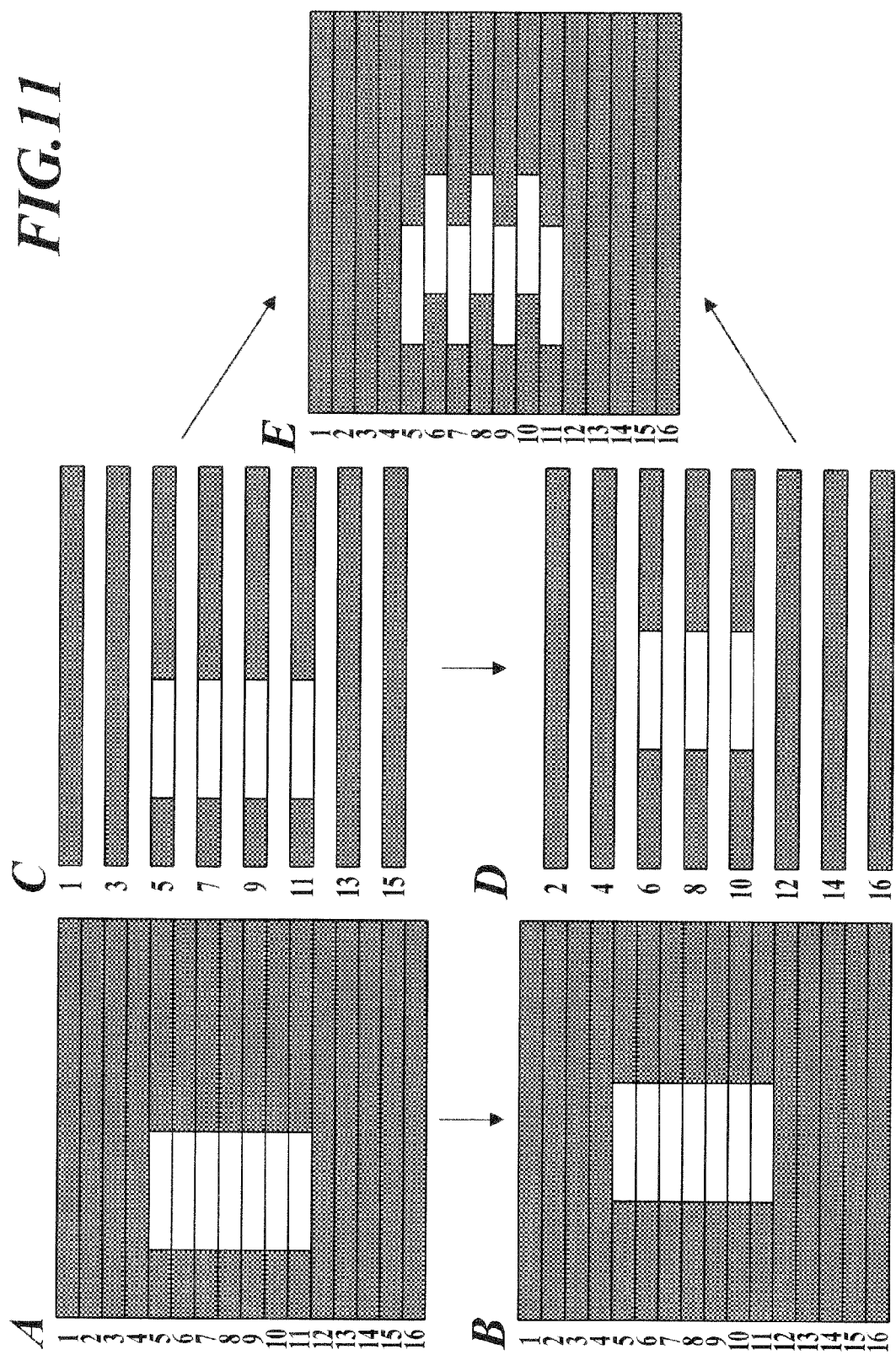
FIG. 11 is a view explaining the synthetic image.

However, in the example shown in FIG. 11, as shown in FIG. 11A and FIG. 11B, the object moves during one frame. Therefore, a positional shift occurs between an image of the object in FIG. 11C and an image of the object in FIG. 11D. Accordingly, when the frame image data obtained in the respective frames are merely synthesized with each other to create the synthetic image data, then as shown in FIG. 11E, comb-like noise (combing noise) is generated.

In this connection, in the first embodiment, the synthetic image data is created with the above-mentioned configuration, whereby the generation of the comb-like noise is suppressed. A specific description is made below while referring to FIG. 12 to FIG. 16.

FIG. 12A, FIG. 12B and FIG. 12C individually show positions of the actual object. Then, FIG. 12B shows a state after elapse of one frame from FIG. 12A, FIG. 12C shows a state after elapse of one frame from FIG. 12B. Moreover, FIG. 12D, FIG. 12E and FIG. 12F individually show frame image data created in the states of FIG. 12A, FIG. 12B and FIG. 12C.

Figure 12:
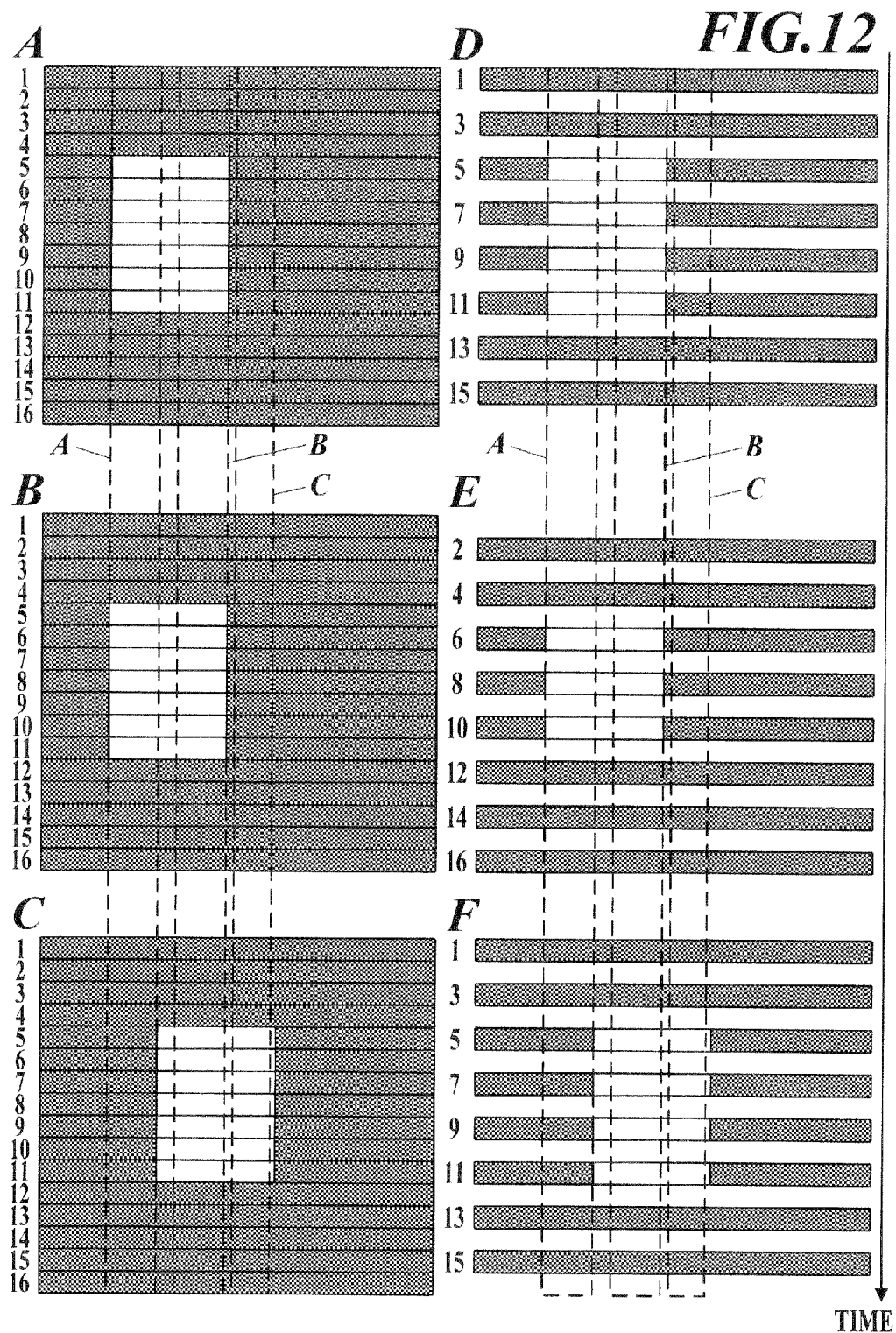
FIG. 12 is a view explaining a relationship between movement of an object and the image data to be created.

Then, as shown in FIG. 12, the object does not move during one frame from the state of FIG. 12A, and turns to the state of FIG. 12B, and moreover, the object moves during one frame from the state of FIG. 12B, and turns to the state of FIG. 12C.

Note that a description is made on the assumption that FIG. 12A and FIG. 12C show odd number frames, and that FIG. 12B shows an even number frame.

Figure 13:
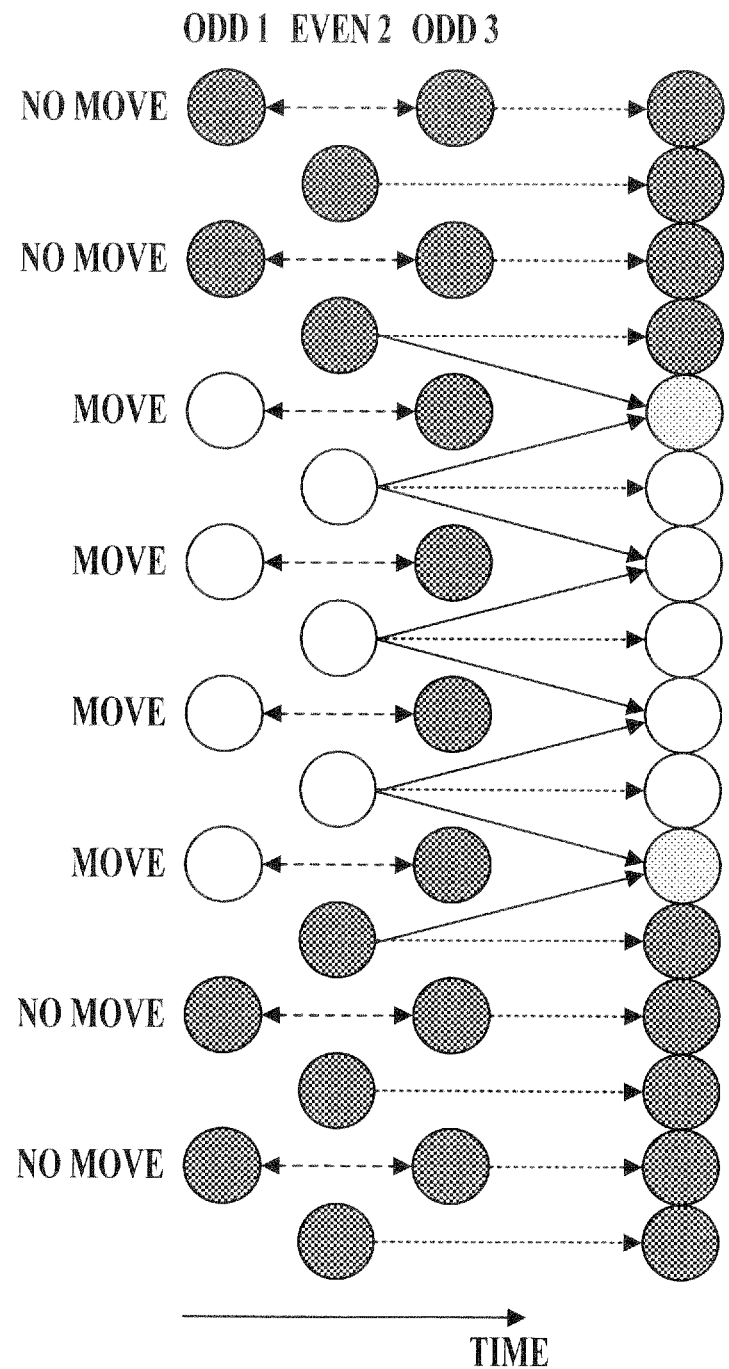
FIG. 13 is a view explaining a creation procedure of the synthetic image.

Then, the generation of the synthetic image data in a portion surrounded by broken lines A in FIG. 12 is performed in accordance with such an aspect as shown in FIG. 13.

Here, with regard to the pixel data of the frame image in the portion of the broken lines A of the first frame, pixels in first, third, thirteenth and fifteenth targets thereof are black, and pixels in fifth, seventh, ninth and eleventh targets thereof are white.

Moreover, with regard to the pixel data of the frame image in the portion of the broken lines A of the second frame, pixels in second, fourth, twelfth, fourteenth and sixteenth targets thereof are black, and pixels in sixth, eighth, tenth targets thereof are white.

Furthermore, with regard to the pixel data of the frame images in the portion of the broken lines A of the third frame, all of pixels in first, third, fifth, seventh, ninth, eleventh, thirteenth and fifteenth targets thereof are black.

First, the frame image data of the first frame and the third frame are compared with each other for each of the pixels, and based on brightness differences therebetween, pixels which move are extracted. That is, as shown in FIG. 13, pixels which have moved in the portion of the broken lines A are the pixels of the fifth, seventh, ninth and eleventh targets.

Then, at the time of creating the synthetic image data, with regard to pixels other than the pixels which have moved, the pixel data of the pixels in the frame image data of the second frame and the pixel data of the pixel in the frame image data of the third frame are directly applied as the synthetic image data.

Moreover, with regard to the pixels which have moved, interpolated pixel data are obtained from the pixel data of the pixels corresponding to the pixels which become adjacent to the pixel concerned in the scanning direction in the event where the synthetic image data is created, and these are applied as the synthetic image data. That is to say, for example, with regard to the pixel of the fifth target, an average of the respective image data of the pixels of the fourth and sixth targets in the frame image data of the second frame is obtained, whereby the interpolated image data is obtained, and this is applied as the pixel data of the pixel of the fifth target in the synthetic image data. Hence, the pixel of the fifth target becomes gray. Also with regard to the pixels of the seventh, ninth and eleventh targets, interpolated pixel data are obtained in a similar way.

Figure 14:
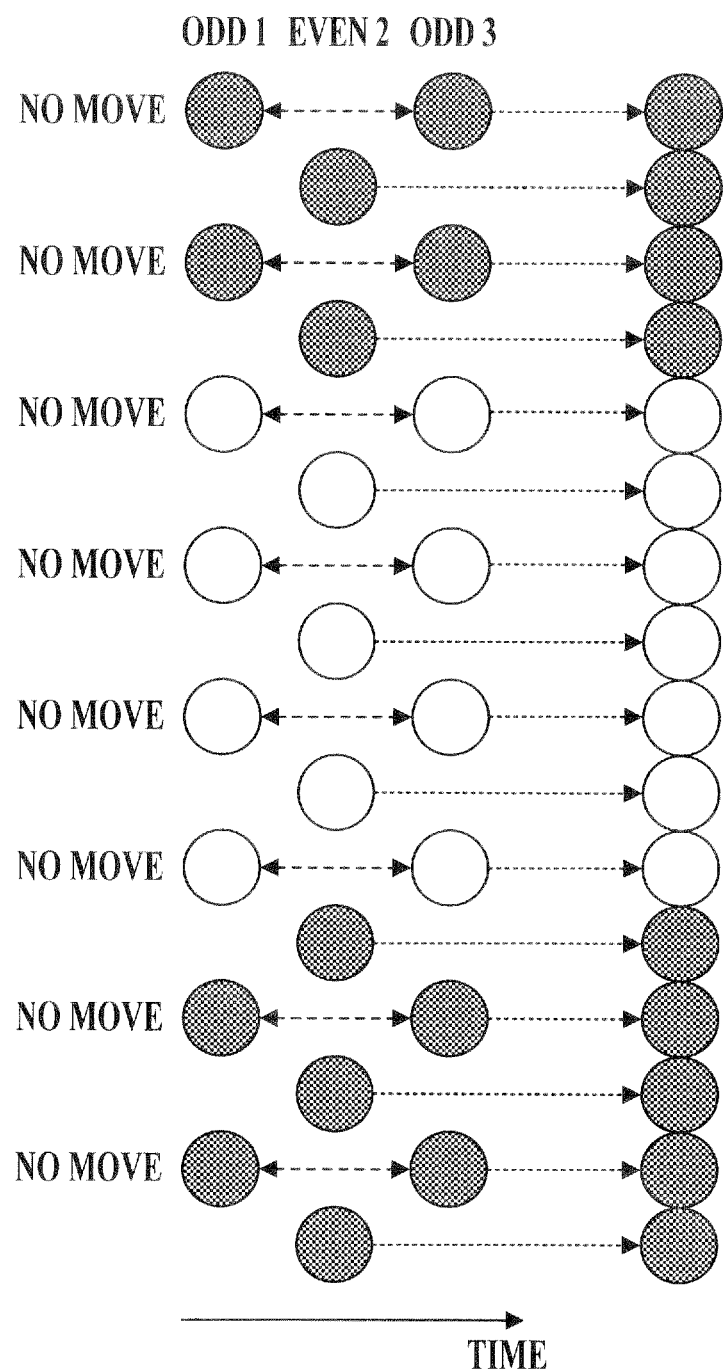
FIG. 14 is a view explaining a creation procedure of the synthetic image.

Moreover, the generation of the synthetic image data in a portion surrounded by broken lines B in FIG. 12 is performed in accordance with such an aspect as shown in FIG. 14.

Here, with regard to the pixel data of the frame image in the portion of the broken lines B of the first frame, the pixels in the first, third, thirteenth and fifteenth targets are black, and the pixels in the fifth, seventh, ninth and eleventh targets are white.

Moreover, with regard to the pixel data of the frame image in the portion of the broken lines B of the second frame, the pixels in the second, fourth, twelfth, fourteenth and sixteenth targets are black, and the pixels in the sixth, eighth, tenth targets are white.

Furthermore, with regard to the pixel data of the frame image in the portion of the broken lines B of the third frame, the pixels in the first, third, thirteenth and fifteenth targets are black, and the pixels in the fifth, seventh, ninth and eleventh targets are white.

In a similar way, the frame image data of the first frame and the third frame are compared with each other for each of the pixels, and based on brightness differences therebetween, pixels which move are extracted. With regard to the portion surrounded by the broken lines B, the pixels which move are not detected, and accordingly, at the time of creating the synthetic image data, for all of the pixels of the first to sixteenth targets, the pixel data of the pixels in the frame image data of the second frame and the pixel data of the pixels in the frame image data of the third frame are directly applied as the synthetic image data.

Figure 15:
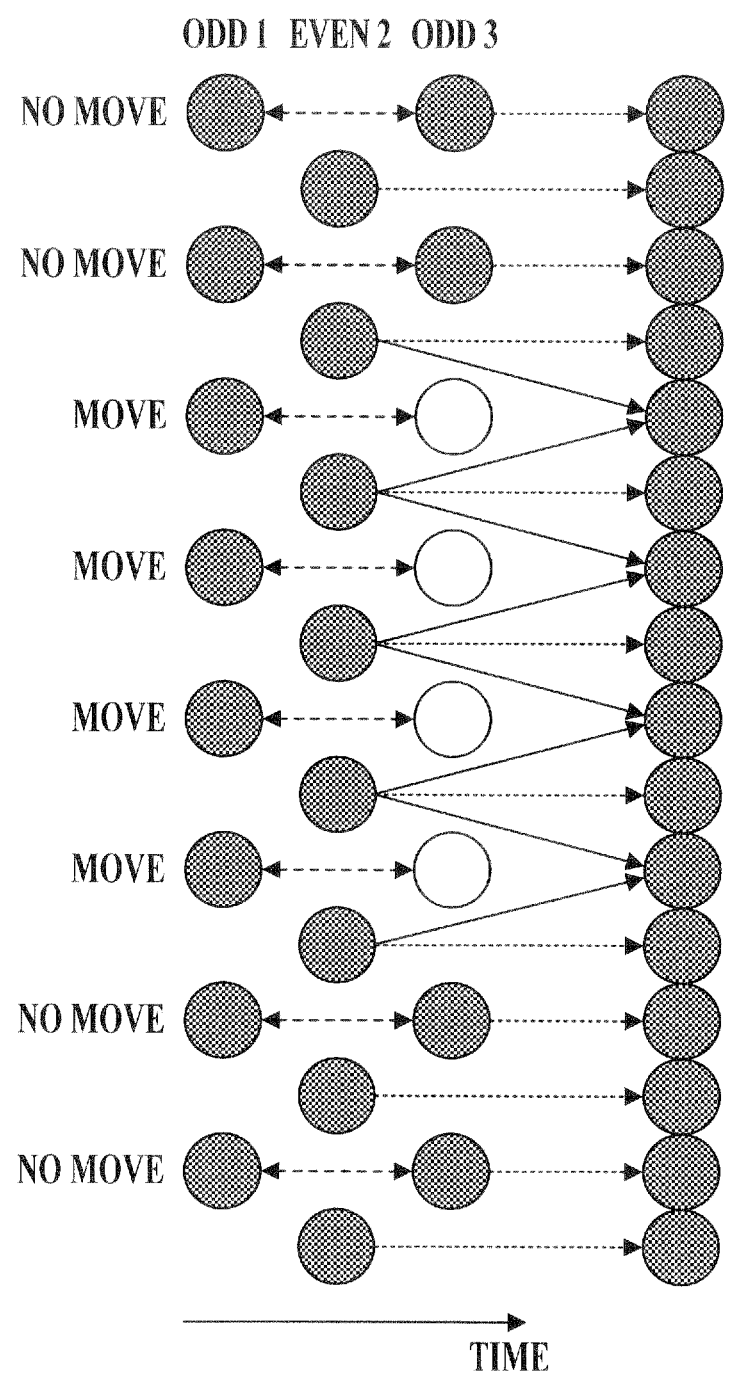
FIG. 15 is a view explaining a creation procedure of the synthetic image.

Moreover, the generation of the synthetic image data in a portion surrounded by broken lines C in FIG. 12 is performed in accordance with such an aspect as shown in FIG. 15.

Here, with regard to the pixel data of the frame image in the portion of the broken lines C of the first frame, all of the pixels in the first, third, fifth, seventh, ninth, eleventh, thirteenth and fifteenth targets are black.

Moreover, with regard to the pixel data of the frame image in the portion of the broken lines C of the second frame, all of the pixels in the second, fourth, sixth, eighth, tenth, twelfth, fourteenth and sixteenth targets are black.

Furthermore, with regard to the pixel data of the frame image in the portion of the broken lines C of the third frame, the pixels in the first, third, thirteenth and fifteenth targets are black, and the pixels in the fifth, seventh, ninth and eleventh targets are white.

In a similar way, the frame image data of the first frame and the third frame are compared with each other for each of the pixels, and based on brightness differences therebetween, pixels which move are extracted. That is to say, as shown in FIG. 15, pixels which have moved in the portion of the broken lines C are the pixels of the fifth, seventh, ninth and eleventh targets. Then, the generation of the synthetic image data is performed in such a manner as mentioned above in FIG. 13.

Figure 16:
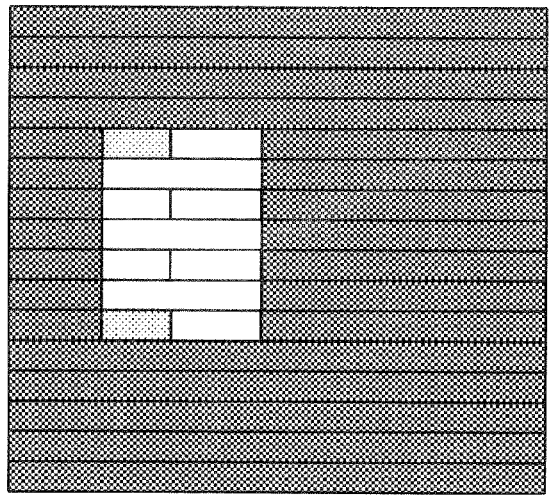
FIG. 16 is a view explaining the synthetic image.

Such processing as described above is performed, whereby synthetic image data as shown in FIG. 16 is created.

As a result, the comb-like noise as shown in FIG. 11E is not generated, and it is made possible to achieve reduction of an artifact.

Second Embodiment

Next, a description is made of a second embodiment of the present invention. Note that the second embodiment of the present invention is similar to the first embodiment except that image data synthesis processing thereof is different from that of the first embodiment, and accordingly, a description is made of the image data synthesis processing according to the second embodiment, and a description of other configurations is omitted.

Figure 17:
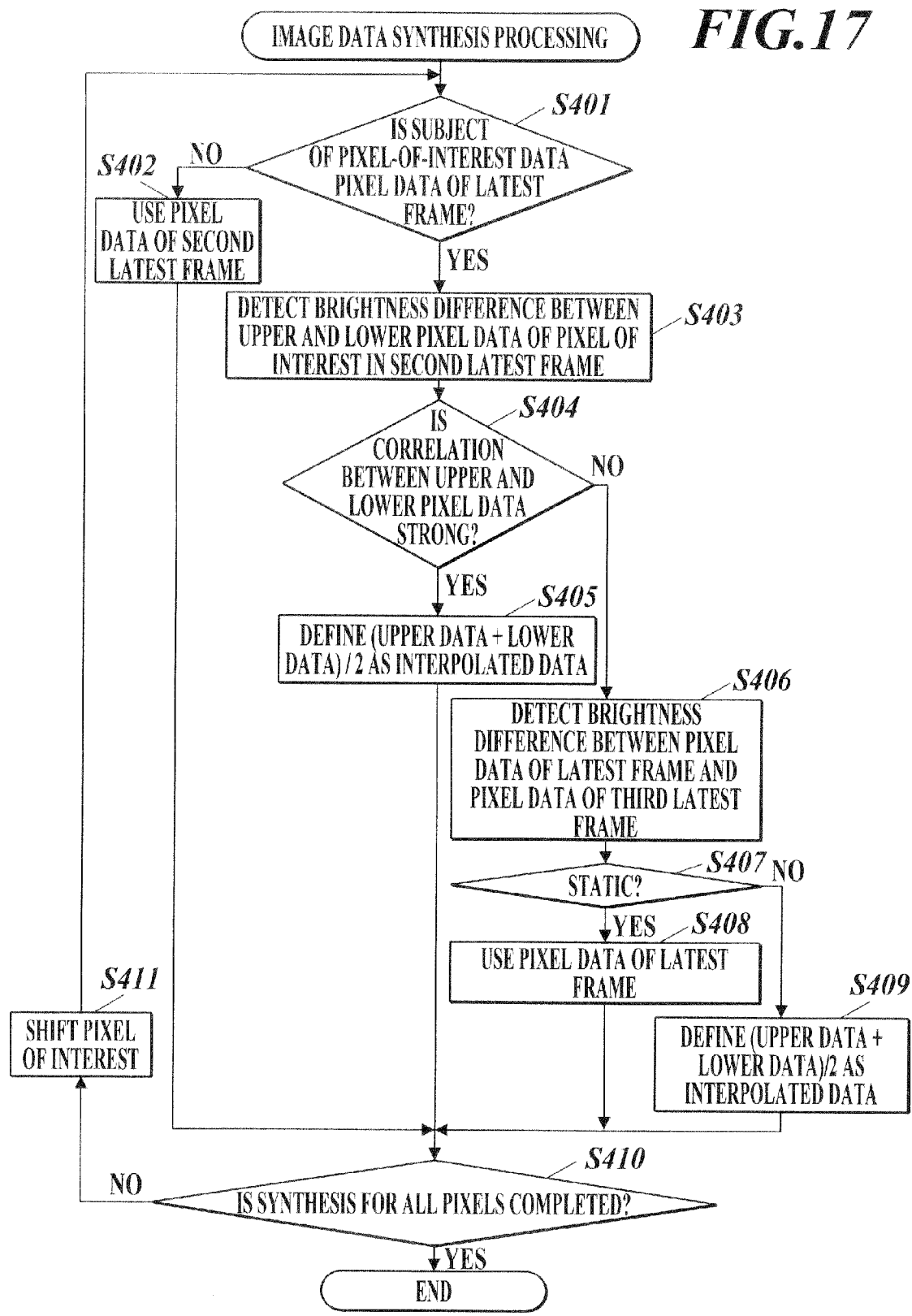
FIG. 17 is a flowchart explaining image data synthesis processing in a second embodiment.

While referring to FIG. 17, a description is made of the image data synthesis processing according to the second embodiment. Note that, in the second embodiment, the selection of the creation method of the pixels by the interpolated data method selection unit 18d is performed by the odd-numbered scan vertical data correlation detection unit 18a, the even-numbered scan vertical data correlation detection unit 18b and the frame difference motion detection unit 18c.

First, in a similar way to the first embodiment, the control unit 18 determines whether or not the subject of the pixel data of the pixel of interest is the pixel data in the frame image data of the latest frame (Step S401). When the control unit 18 does not determine that the subject of the pixel data of the pixel of interest is the pixel data in the frame image data of the latest frame (Step S401: N), the control unit 18 uses, as the pixel data of the pixel of interest, the pixel data in the frame image data of the second latest frame (Step S402).

Meanwhile, when the control unit 18 determines that the subject of the pixel data of the pixel of interest is the pixel data in the frame image data of the latest frame (Step S401: Y), then by functions of the odd-numbered scan vertical data correlation detection unit 18a and the even-numbered scan vertical data correlation detection unit 18b, the control unit 18 extracts the pixel data (vertical pixel data) of the pixels, which correspond to the pixels adjacent to the pixel of interest in the vertical direction (scanning direction), from the frame image data of the second latest frame, and detects a brightness difference between the extracted pixels in such a manner as mentioned above (Step S403).

Then, the control unit 18 determines whether or not a correlation between the vertical pixel data is strong as a result of detecting the brightness difference (Step S404).

When the control unit 18 determines that the correlation between the vertical pixel data is strong (S404: Y), then by the functions of the interpolated data method selection unit 18d and the interpolated data selection unit 18e, the control unit 18 writes interpolated data, which is created by obtaining an average of the vertical pixel data, as the pixel data of the pixel of interest into the work area of the memory unit 15 (Step S405). Meanwhile, when the control unit 18 does not determine that the correlation between the vertical pixel data is strong (Step S404: N), the control unit 18 executes processing of Step S406 and after. Contents of the processing of Step S406 and after are similar to contents of the processing of Step S303 to Step S308 of FIG. 7, and accordingly, a description thereof is omitted.

Next, while referring to FIG. 18 to FIG. 21, a specific description is made of a creation process of the synthetic image data in the second embodiment. Note that the obtaining conditions of the frame image data and the positions of the pixels in the synthetic image data, which are used in the description, are assumed to be similar to those in the description of FIG. 12.

Figure 18:
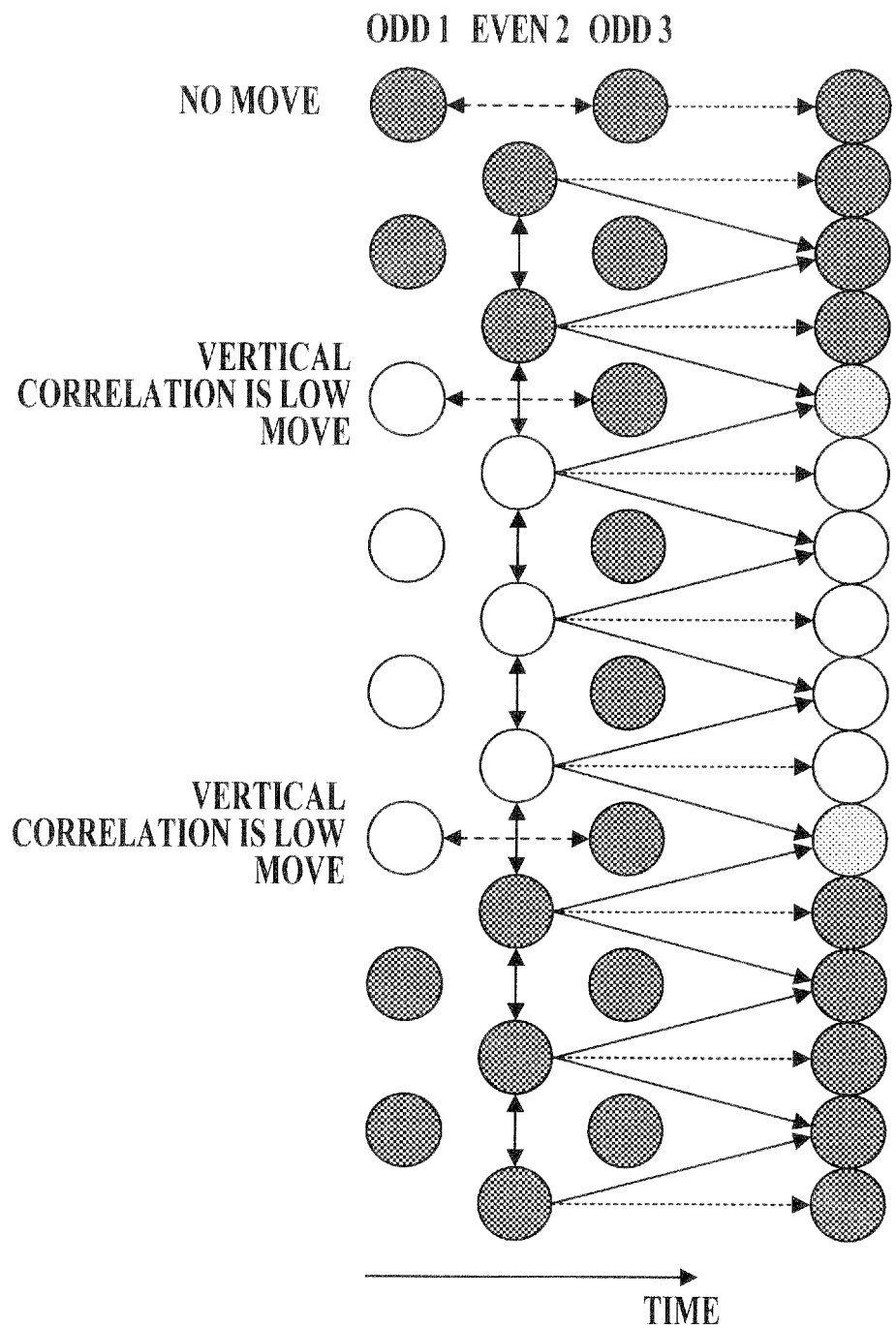
FIG. 18 is a view explaining a creation procedure of a synthetic image.

In the second embodiment, the generation of the synthetic image data in the portion surrounded by the broken lines A in FIG. 12 is performed in accordance with an aspect shown in FIG. 18.

First, the vertical pixel data as pixel data of the pixels, which correspond to the pixels adjacent to the pixel of interest in the vertical direction, are extracted. That is to say, for example, if the pixel of interest is the pixel of the third target, then the pixel data to be extracted as the vertical pixel data are the pixel data of the pixels of the second and fourth targets in the frame image data of the second frame. Moreover, if the pixel of interest is the pixel of the fifth target, then the pixel data to be extracted as the vertical pixel data are the pixel data of the pixels of the fourth and sixth targets in the frame image data of the second frame.

Then, the brightness difference between the vertical pixel data is detected to determine strength of the correlation. In the case where the correlation is strong, then the interpolated pixel data is obtained from the vertical pixel data, and this is applied as the pixel data of the pixel of interest to the synthetic image data. That is to say, for example, with regard to the pixel of the third target, since a correlation between the respective pixel data of the pixels of the second and fourth targets is strong, an average of these pixel data is obtained, whereby the interpolated pixel data is obtained, and this is applied as the pixel data of the pixel of the third target in the synthetic image data.

Meanwhile, in the case where the correlation between the vertical pixel data is not strong, then it is further determined whether or not the pixel of interest has moved. Note that, since a method of determining such a motion is similar to that of the first embodiment, a detailed description thereof is omitted. For example, with regard to the pixel of the fifth target, a correlation between the respective pixel data of the pixels of the fourth and sixth targets in the frame image data of the second frame is not strong (is low), and accordingly, the motion determination is performed for the pixel of interest. Then, since the pixel of interest has moved, an average of the vertical image data is obtained to obtain interpolated pixel data, and this is applied as pixel data of the pixel of the fifth target in the synthetic image data. Hence, the pixel of the fifth target becomes gray.

Figure 19:
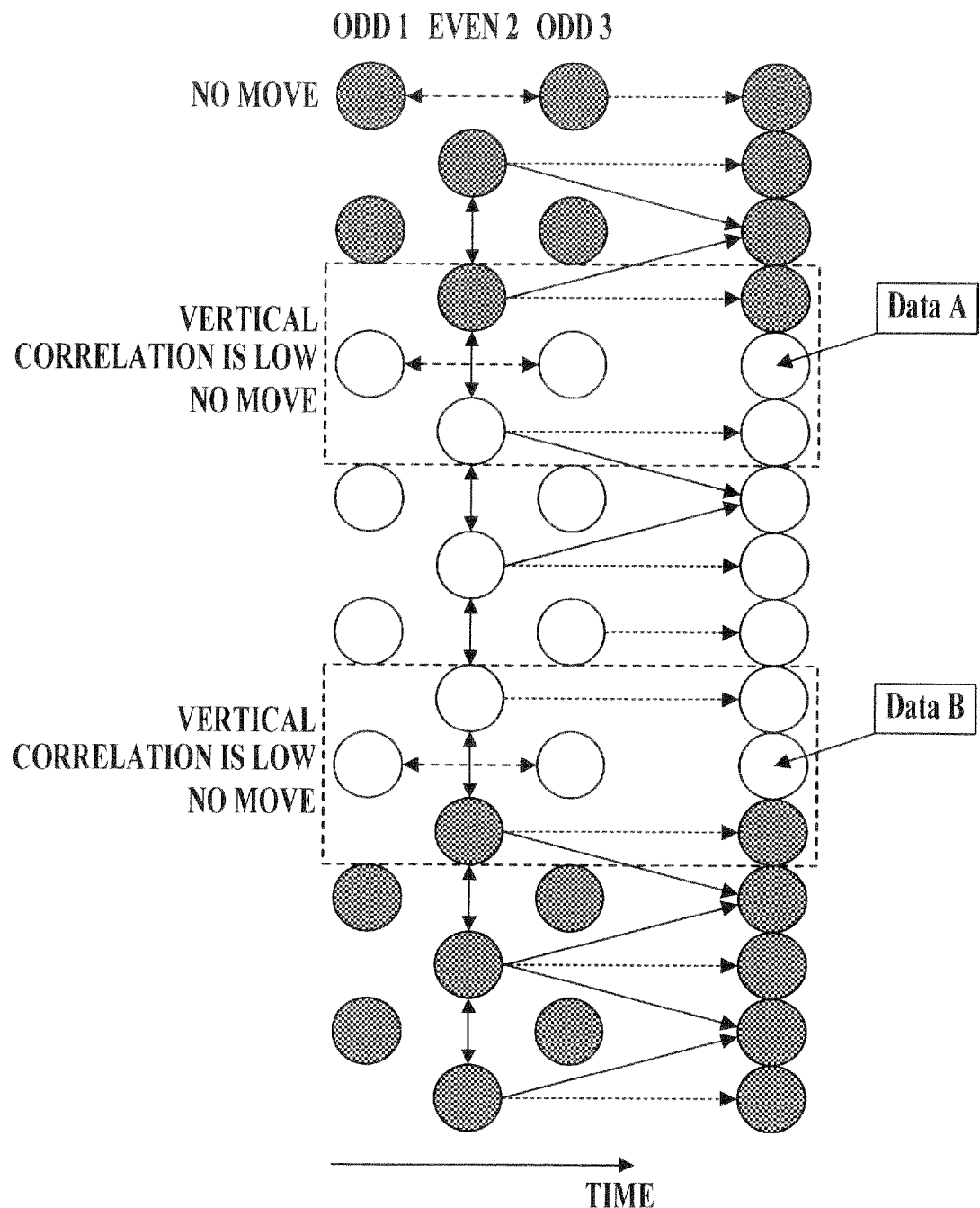
FIG. 19 is a view explaining a creation procedure of the synthetic image.

Moreover, with regard to the creation of the synthetic image data in the portion surrounded by the broken lines B in FIG. 12, as shown in FIG. 19, the creation of the synthetic image data is performed by a similar process.

Here, with regard to each of pixels denoted by "Data A" and "Data B" in FIG. 19, pixel data is obtained as shown in FIG. 20A. That is to say, with regard to the pixel of the fifth target, which is the pixel of interest and is denoted by "Data A", a correlation between the respective pixel data of the pixels of the fourth and sixth targets in the frame image data of the second frame is low, and accordingly, the motion determination is performed for the pixel of interest. Then, since the pixel of interest has not moved, pixel data of a pixel (pixel denoted by "1" in FIG. 20A) in the frame image data of the third frame is directly applied as the synthetic image data. In FIG. 19, also with regard to the pixel of the eleventh target, which is the pixel of interest and is denoted by "Data B", pixel data is obtained in a similar way.

Note that, with regard to the pixel data of each of the pixels denoted by "Data A" and "Data B", a similar effect is obtained even if such aspects as shown in FIG. 20B and FIG. 20C are used as well as the aspect shown in FIG. 20A. That is to say, in the aspect shown in FIG. 20B, pixel data of the pixel (pixel denoted by "0" in FIG. 20B) in the frame image data of the first frame is directly applied as the synthetic image data. Moreover, in the aspect shown in FIG. 20C, one obtained by averaging the pixel data of the pixel (pixel denoted by "0" in FIG. 20C) in the frame image data of the first frame and the pixel data of the pixel (pixel denoted by "1" in FIG. 20C) in the frame image data of the third frame is applied as the synthetic image data.

Figure 21:
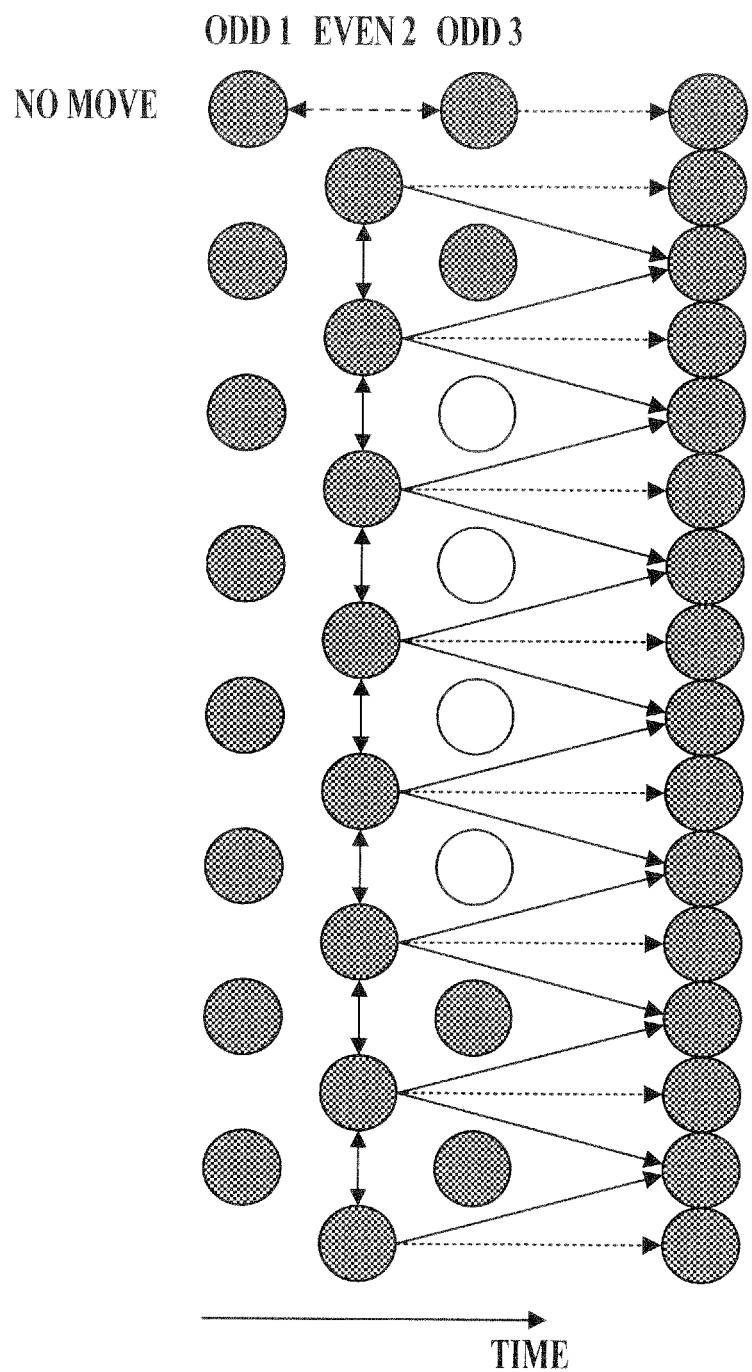
FIG. 21 is a view explaining a creation procedure of the synthetic image.

Moreover, with regard to the creation of the synthetic image data in the portion surrounded by the broken lines C in FIG. 12, as shown in FIG. 21, the creation of the synthetic image data is performed by a similar process to that mentioned above.

Note that, with regard to the pixel of the first target as an upper end portion of the frame image, the motion detection by the brightness difference, which is as shown in the first embodiment, is performed, whereby the creation of the pixel data is performed; however, the pixel data of the pixel of the second target in the frame image data of the second frame may be applied. Moreover, in the case where the latest frame is an even number frame, with regard to the pixel of the sixteenth target as a lower end portion of the frame image, pixel data of the pixel of the fifteenth target in an odd number frame as the second latest frame may be applied.

As described above, also by the second embodiment, a similar effect to that of the first embodiment is obtained.

Third Embodiment

Next, a description is made of a third embodiment of the present invention. Note that the third embodiment of the present invention is similar to the first and second embodiments except that image data synthesis processing thereof is different from those of the first and second embodiments, and accordingly, a description is made of the image data synthesis processing according to the third embodiment, and a description of other configurations is omitted.

Figure 22:
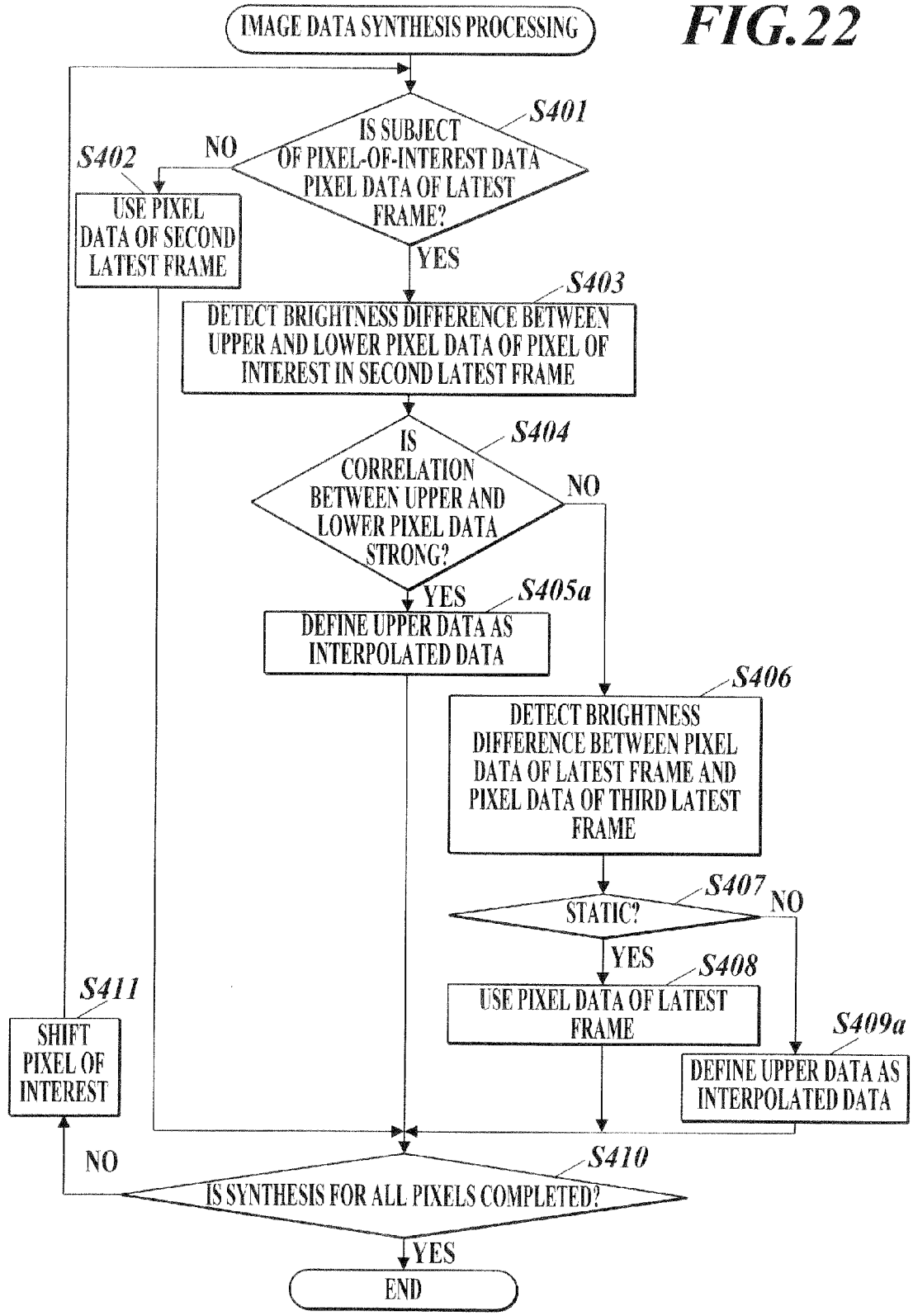
FIG. 22 is a flowchart explaining image data synthesis processing in a third embodiment.

While referring to FIG. 22, a description is made of the image data synthesis processing according to the third embodiment. Here, a description is made of Step S405a and Step S409a, which are different from equivalent steps in the image data synthesis processing according to the second embodiment, and since pieces of processing in other steps are similar to equivalent pieces in the image data synthesis processing according to the second embodiment, a description thereof is omitted.

In Step S405a, the control unit 18 writes upper pixel data between the vertical pixel data as the interpolated data into the work area of the memory unit 15 (Step S405a). That is to say, when illustration is made with reference to FIG. 18, then with regard to the pixel of interest, which is the pixel of the third target, the pixel data of the pixel of the second target between the respective pixel data (vertical pixel data) of the pixels of the second and fourth targets in the frame image data of the second frame is directly applied as the pixel data of the pixel of the third target.

Moreover, in a similar way also in Step S409a, the control unit 18 writes upper pixel data between the vertical pixel data as the interpolated data into the work area of the memory unit 15 (Step S409a). That is to say, when illustration is made with reference to FIG. 18, then with regard to the pixel of interest, which is the pixel of the fifth target, the pixel data of the pixel of the fourth target between the respective pixel data (vertical pixel data) of the pixels of the fourth and sixth targets in the frame image data of the second frame is directly applied as the pixel data of the pixel of the fifth target. Hence, in the third embodiment, the pixel of the fifth target becomes black, and meanwhile, the pixel of the eleventh target becomes white as a result of performing similar processing.

Note that, in place of Step S409a, Step S409 of the image data synthesis processing shown in FIG. 17 may be executed.

Figure 23:
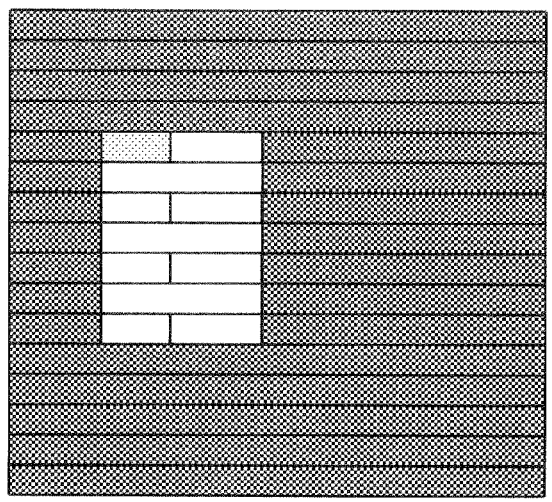
FIG. 23 is a view explaining a synthetic image.

The processing as described above is performed, whereby such synthetic image data as shown in FIG. 23 is created.

As described above, in accordance with the third embodiment, the comb-like noise is not generated, and it is made possible to achieve the reduction of the artifact. Moreover, more than in the case of obtaining the interpolated data by averaging the vertical pixel data, it is made possible to reduce a processing load, or alternatively, to simplify the circuit configuration in the case of realizing the processing by hardware, and a reduction of cost can be achieved.

Fourth Embodiment

Next, a description is made of a fourth embodiment of the present invention. Note that the fourth embodiment of the present invention is similar to the first and second embodiments except that image data synthesis processing thereof is different from those of the first and second embodiments, and accordingly, a description is made of the image data synthesis processing according to the fourth embodiment, and a description of other configurations is omitted.

Figure 24:
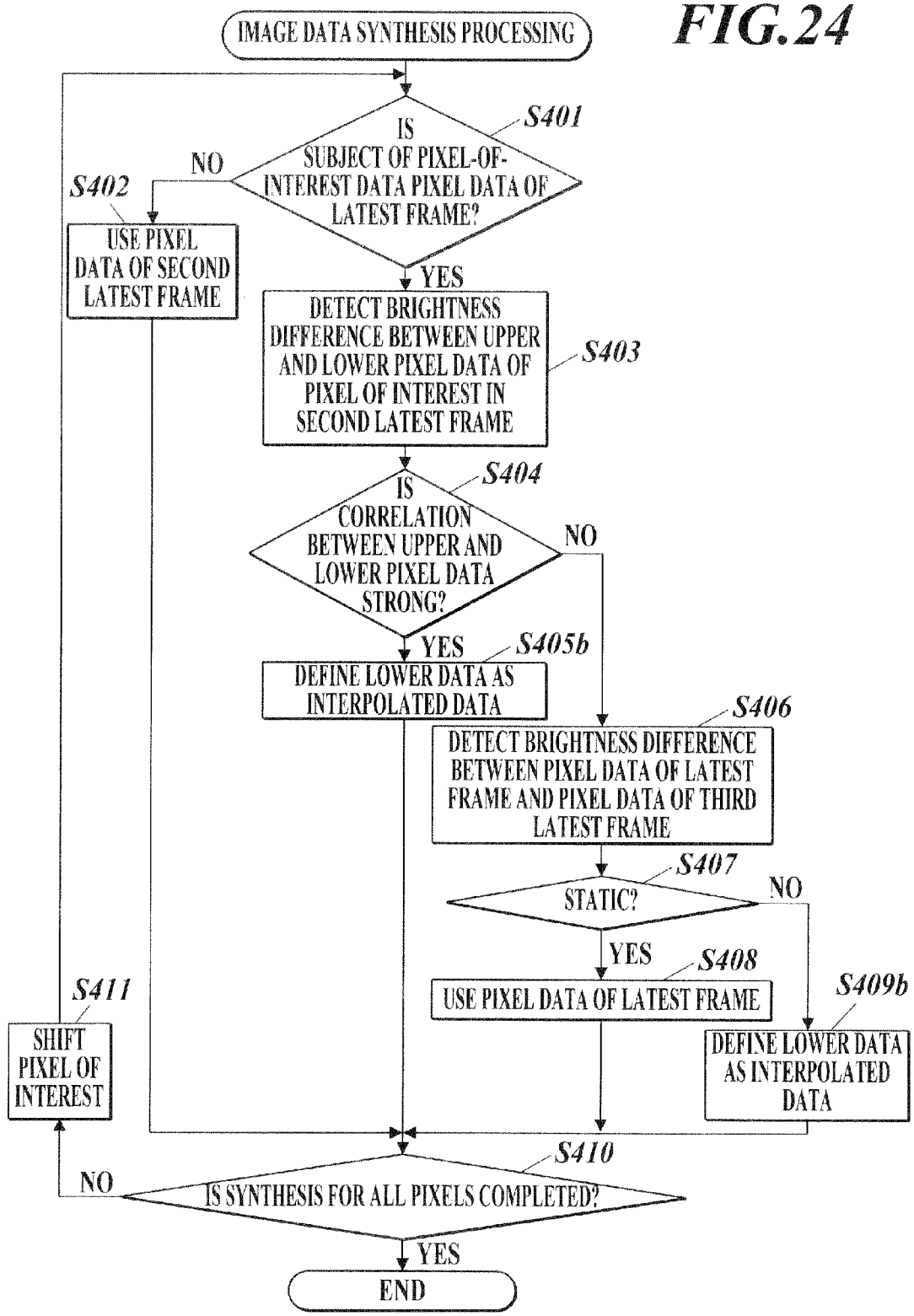
FIG. 24 is a flowchart explaining image data synthesis processing in a fourth embodiment.

While referring to FIG. 24, a description is made of the image data synthesis processing according to the fourth embodiment. Here, a description is made of Step S405b and Step S409b, which are different from equivalent steps in the image data synthesis processing according to the second embodiment, and since pieces of processing in other steps are similar to equivalent pieces in the image data synthesis processing according to the second embodiment, a description thereof is omitted.

In Step S405b, the control unit 18 writes lower pixel data between the vertical pixel data as the interpolated data into the work area of the memory unit 15 (Step S405b). That is to say, when illustration is made with reference to FIG. 18, then with regard to the pixel of interest, which is the pixel of the third target, the pixel data of the pixel of the fourth target between the respective pixel data (vertical pixel data) of the pixels of the second and fourth targets in the frame image data of the second frame is directly applied as the pixel data of the pixel of the third target.

Moreover, in a similar way also in Step S409b, the control unit 18 writes lower pixel data between the vertical pixel data as the interpolated data into the work area of the memory unit 15 (Step S409b). That is to say, when illustration is made with reference to FIG. 18, then with regard to the pixel of interest, which is the pixel of the fifth target, the pixel data of the pixel of the sixth target between the respective pixel data (vertical pixel data) of the pixels of the fourth and sixth targets in the frame image data of the second frame is directly applied as the pixel data of the pixel of the fifth target. Hence, in the fourth embodiment, the pixel of the fifth target becomes white, and meanwhile, the pixel of the eleventh target becomes black as a result of performing similar processing.

Note that, in place of Step S409b, Step S409 of the image data synthesis processing shown in FIG. 17 may be executed.

Figure 25:
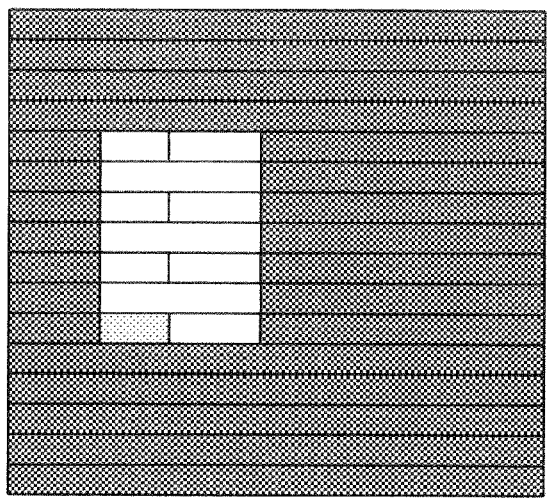
FIG. 25 is a view explaining a synthetic image.
Figure 26:
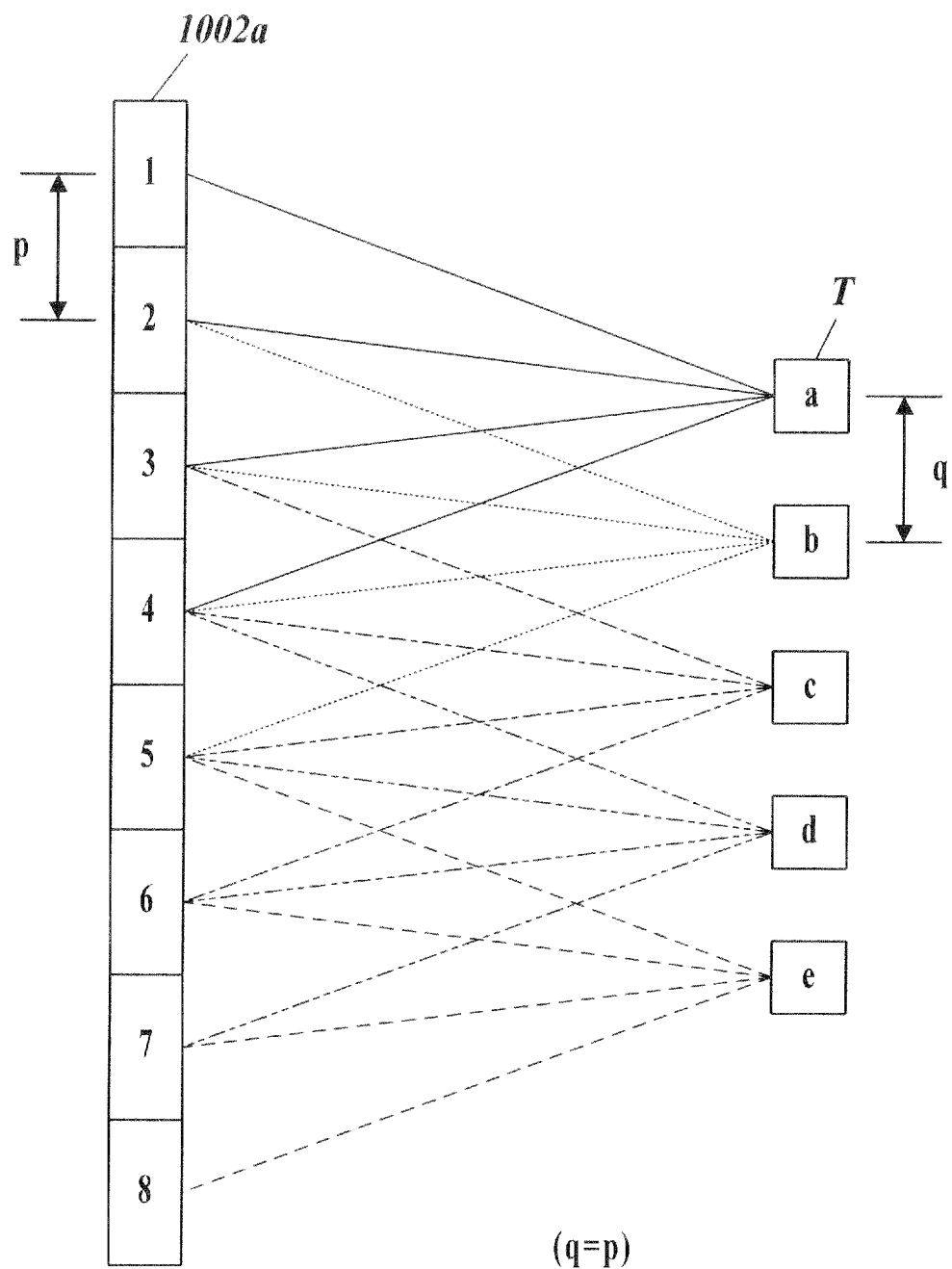
FIG. 26 is a view explaining operations of a conventional ultrasound diagnostic device.
Figure 27:
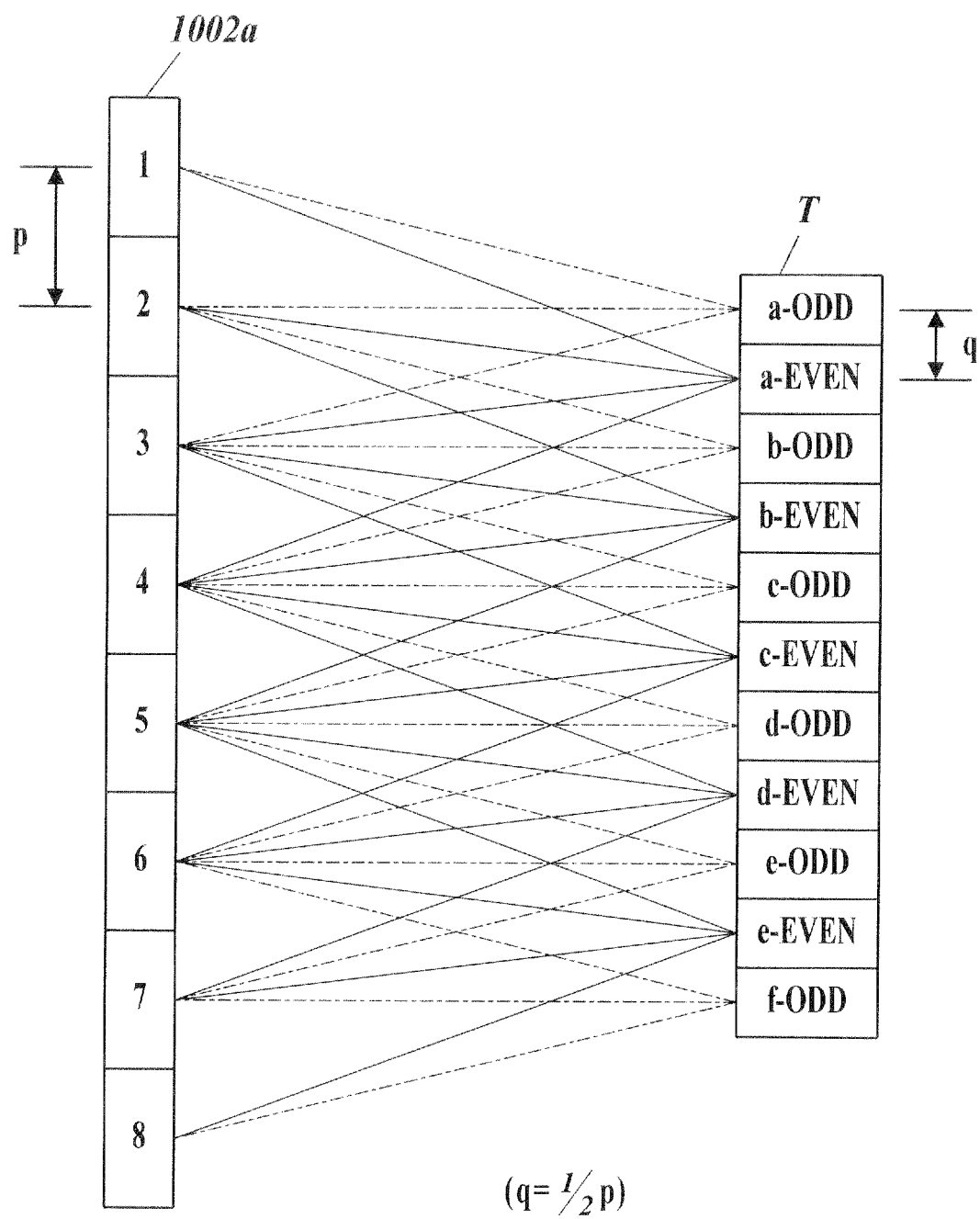
FIG. 27 is a view explaining operations of a conventional ultrasound diagnostic device.

The processing as described above is performed, whereby such synthetic image data as shown in FIG. 25 is created. As described above, in accordance with the fourth embodiment, a similar effect to that of the third embodiment can be exerted.

As described above, in accordance with the first to fourth embodiments of the present invention, the ultrasound probe 2 includes the n pieces of transducers 2a while arranging the transducers 2a in parallel, the transducers 2a outputting the transmitted ultrasound waves toward the test body by the drive signal, and in addition, outputting the received signals by receiving the reflected ultrasound waves from the test body. Then, the transmitter unit 12 supplies the drive signal to the selected transducers 2a among the n pieces. Then, the receiver unit 13 receives the received signals to be outputted from the selected transducers 2a. Then, the control unit 18 sequentially selects the transducers 2a, which are to be supplied with the drive signal, while shifting the transducers 2a by a predetermined number in the array direction every time when each of the transmitted ultrasound waves is outputted. Then, based on the received signals sequentially received by the receiver unit 13, the image creation unit 14 creates the image data of the inside of the test body for each of the frames. Then, while making switch for each of the frames, the control unit 18 executes the selection of the m pieces of the transducers 2a arranged consecutively and the selection of the m+1 pieces of the transducers 2a arranged consecutively. Then, every time when the image data of each of the frames is created, the control unit 18 at least creates the synthetic image data obtained by synthesizing the image data of the two consecutive frames with each other. As a result, the interval between the targets, which depends on the interval between the transducers, can be reduced, and accordingly, the resolution can be enhanced. In addition, the scanning is performed while changing the number of driven transducers, which perform the transmission/reception, to the odd number/even number for each of the frames, and accordingly, the lowering of the frame rate can be suppressed.

Moreover, in accordance with the first to fourth embodiments of the present invention, the memory unit 15 at least stores the image data of the range from the latest frame between the two consecutive frames to the third latest frame. Then, the control unit 18 creates the pixel data of the pixel in the synthetic image data, which corresponds to a changed portion of the pixel between the image data of the latest frame and the image data of the third latest frame, based on the pixel data in the image data of the second latest frame, which corresponds to the pixels adjacent to the pixel concerned. As a result, it is made possible to suppress the generation of the comb-like noise, and accordingly, the artifact can be reduced.

Moreover, in accordance with the first and second embodiments, the control unit 18 sets the pixel data of the pixel in the synthetic image data, which corresponds to the changed portion of the pixel, to the one obtained by the interpolation from the pixel data in the image data of the second latest frame, which individually correspond to the pixels adjacent to both sides of the pixel concerned in the azimuth direction. As a result, the generation of the comb-like noise is suppressed, and in addition, image data more approximate to such a measurement subject can be obtained, and accordingly, enhancement of image quality can be achieved in addition to the reduction of the artifact.

Moreover, in accordance with the first to fourth embodiments of the present invention, the control unit 18 sets the pixel data of the pixel in the synthetic image data, which corresponds to the changed portion of the pixel, to the same one as the pixel data in the image data of the second latest frame, which corresponds to the pixel adjacent to either side of the pixel concerned in the azimuth direction. As a result, it is made possible to suppress the generation of the comb-like noise, and accordingly, the artifact can be reduced. Furthermore, a special calculation and the like for obtaining the pixel data are not necessary, and the processing is simplified, or alternatively, can be realized by a simple circuit configuration, whereby the reduction of the cost is achieved. Moreover, the image can be displayed more clearly and distinctively, and accordingly, the enhancement of the image quality can also be achieved.

Moreover, in accordance with the first embodiment of the present invention, the control unit 18 sets the pixel data of the pixel in the synthetic image data, which corresponds to the portion where there is no change in the pixel between the image data of the latest frame and the pixel data of the third latest frame, to the pixel data of the pixel in the image data of the latest frame, which corresponds to the pixel concerned. As a result, a special calculation and the like for obtaining the pixel data are not necessary, and the processing is simplified, or alternatively, can be realized by a simple circuit configuration, whereby the reduction of the cost is achieved.

Moreover, in accordance with the second to fourth embodiments of the present invention, the control unit 18 determines whether or not the two pixels adjacent to each other in the azimuth direction in the image data of the second latest frame, which serve as the determination subject pixels, satisfy a predetermined correlation condition. Then, when the correlation condition is satisfied as a result of the determination, the control unit 18 sets the pixel data of the pixel arranged between the two pixels in the synthetic image data, which correspond to the determination subject pixels, to the one created based on the pixel data related to the determination subject pixels concerned. As a result, the creation aspect of the pixel data is decided by determining the correlation, and accordingly, the simplification of the processing can be achieved, or alternatively, it is made possible to realize the processing by a simple circuit configuration, whereby the reduction of the cost is achieved.

Moreover, in accordance with the second to fourth embodiments of the present invention, the control unit 18 determines, as a correlation condition, whether or not the brightness difference between the determination subject pixels is a predetermined threshold value or less, and accordingly, the determination of the correlation condition can be performed with ease.

Note that the description in the embodiments of the present invention merely illustrates examples of the ultrasound diagnostic device according to the present invention, and the ultrasound diagnostic device according to the present invention is not limited to this. Detailed configurations and detailed operations of the respective functional units which compose the ultrasound diagnostic device are also changeable as appropriate.

Moreover, in this embodiment, the odd number scanning unit 13*b* and the even number scanning unit 13*c* are formed in the one receiver unit 13; however, such a configuration may be adopted, in which a plurality of the receiver units are provided, and the odd number scanning unit 13*b* and the even number scanning unit 13*c* are individually provided in the receiver units separate from each other.

Moreover, in this embodiment, the odd-numbered scan B-mode image creation unit 14*a* and the even-numbered scan B-mode image creation unit 14 are formed in the one image creation unit 14; however, such a configuration may be adopted, in which a plurality of the image creation units 14 are provided, and the odd-numbered scan B-mode image creation unit 14*a* and the even-numbered scan B-mode image creation unit 14*b* are individually provided in the image creation units separate from each other.

Moreover, in this embodiment, the odd-numbered scan B-mode image data memory unit 15*a* and the even-numbered scan B-mode image data memory unit 15*b* are formed in the one memory unit 15; however, such a configuration may be adopted, in which a plurality of the memory units are provided, and the odd-numbered scan B-mode image data memory unit 15*a* and the even-numbered scan B-mode image data memory unit 15*b* are individually provided in the memory units separate from each other.

Moreover, in the first embodiment, in the case where the pixel of interest moves, then the average of the pixel data of the pixels corresponding to the pixels adjacent thereto in the vertical direction is obtained to create the interpolated data; however, as in the third or fourth embodiment, the upper data or the lower data may be used as the interpolated data. Moreover, these may be used in combination with each other.

Moreover, in this embodiment, the determination of the brightness difference is performed for each of the pixels, and the motion is detected; however, for example, such a configuration may be adopted, in which a plurality of pixels composed of x×y pieces (each of x and y is an integer of one or more) are defined as a unit of block, brightness averages are obtained for each of the blocks, and values of the averages are compared with one another to determine the brightness difference, and the motion detection is performed. In such a way, a reduction of an arithmetic operation amount can be achieved, and moreover, in the case where noise is superimposed, this can be absorbed. Accordingly, even in the case where the noise is generated, it is made possible to reduce an influence thereof.

Moreover, in the second to fourth embodiments, the correlation between the pixels is determined from the brightness difference between the vertical pixel data; however, such a configuration may be adopted, in which a plurality of pixels composed of x×y pieces (each of x and y is an integer of one or more) are defined as a unit of block, brightness averages are obtained for each of the blocks, and values of these averages are compared with each other between the upper and lower blocks to determine the brightness difference, and the determination is performed between the upper and lower blocks. Then, from a result of such a correlation determination, the interpolated pixel data may be obtained based on the respective average values of the upper and lower blocks for the pixel of the target arranged between these blocks or for the plurality of pixels turned to the unit of block. In such a way, the reduction of the arithmetic operation amount can be achieved, and moreover, in the case where noise is superimposed, this can be absorbed. Accordingly, even in the case where the noise is generated, it is made possible to reduce the influence thereof.

Moreover, in this embodiment, the example is disclosed, where a hard disk, a semiconductor nonvolatile memory or the like is used as a medium capable of reading a program according to the present invention by a computer; however, the present invention is not limited to this example. As another computer-readable medium, a portable recording medium such as a CD-ROM is applicable. Moreover, a carrier wave is also applied as a medium that provides data of the program according to the present invention through a communication line.

INDUSTRIAL APPLICABILITY

The present invention is applicable in the field (particularly, the medical field) where the diagnosis is performed by the ultrasound image.

EXPLANATION OF REFERENCE NUMERALS

S ULTRASOUND DIAGNOSTIC DEVICE
1 ULTRASOUND DIAGNOSTIC DEVICE BODY
2 ULTRASOUND PROBE
2a TRANSDUCER
12 TRANSMITTER UNIT
13 RECEIVER UNIT
14 IMAGE CREATION UNIT
15 MEMORY UNIT
17 DISPLAY UNIT
18 CONTROL UNIT

The invention claimed is:

1. An ultrasound diagnostic device comprising:
an ultrasound probe which includes n pieces of transducers being arranged in parallel, n satisfying n>1, the transducers outputting transmitted ultrasound waves toward a test body by a drive signal, and outputting received signals by receiving reflected ultrasound waves from the test body;
a transmitter unit which supplies the drive signal to selected transducers from among the n pieces of transducers;
a receiver unit which receives received signals to be outputted from the selected transducers;
a control unit which sequentially selects the transducers to be supplied with the drive signal from among the n pieces of transducers, wherein the control unit shifts the transducers to be selected by a predetermined number in an array direction every time when each of the transmitted ultrasound waves is outputted; and
an image processing unit which creates image data of an inside of the test body for each of a plurality frames based on the received signals sequentially received by the receiver unit,
wherein the control unit switches a number of the transducers which are sequentially selected to be supplied with the drive signal for consecutive frames, by executing sequential selection of m pieces of the transducers arranged consecutively for a first frame and executing sequential selection of m+1 pieces of the transducers arranged consecutively for a second frame which is consecutive to the first frame, m satisfying m<n, and
wherein every time when the image data of each frame is created, the control unit creates synthetic image data obtained by synthesizing image data of at least two consecutive frames with each other.

2. The ultrasound diagnostic device according to claim 1, further comprising:
a storage unit which at least stores image data of a range from a latest frame among the two consecutive frames to a third latest frame,
wherein the control unit creates pixel data of a pixel in the synthetic image data, the created pixel data corresponding to a changed portion where a pixel changed between image data of the latest frame and image data of the third latest frame, based on pixel data in image data of a second latest frame, the pixel data in the image data of the second latest frame corresponding to a pixel adjacent to the changed portion where the pixel changed between the image data of the latest frame and the image data of the third latest frame.

3. The ultrasound diagnostic device according to claim 2, wherein the control unit determines whether or not two pixels adjacent to each other in an azimuth direction in the image data of the second latest frame, the two pixels serving as determination subject pixels, satisfy a predetermined correlation condition, and when the correlation condition is satisfied as a result of the determination, the control unit sets pixel data of a pixel to be arranged between two pixels in the synthetic image, the two pixels corresponding to the determination subject pixels, to pixel data created based on pixel data related to the determination subject pixels.

4. The ultrasound diagnostic device according to claim 3, wherein the control unit determines, as the correlation condition, whether or not a brightness difference between the determination subject pixels is a predetermined threshold value or less.

5. The ultrasound diagnostic device according to claim 2, wherein the control unit sets pixel data of a pixel in the synthetic image data, the pixel data corresponding to a portion where a pixel did not change between the image data of the latest frame and the image data of the third latest frame, to pixel data of a pixel in the image data of the latest frame corresponding to the portion where the pixel did not change between the image data of the latest frame and the image data of the third latest frame.

6. The ultrasound diagnostic device according to claim 2, wherein the control unit sets the pixel data of the pixel in the synthetic image data, the pixel data corresponding to the changed portion, to pixel data obtained by interpolation from the pixel data in the image data of the second latest frame, the pixel data in the image data of the second latest frame individually corresponding to pixels adjacent in an azimuth direction to both sides of the changed portion where the pixel changed between the image data of the latest frame and the image data of the third latest frame.

7. The ultrasound diagnostic device according to claim 6, wherein the control unit sets pixel data of a pixel in the synthetic image data, the pixel data corresponding to a portion where a pixel did not change between the image data of the latest frame and the image data of the third latest frame, to pixel data of a pixel in the image data of the latest frame, the pixel data corresponding to the portion where there is no change of the pixel did not change between the image data of the latest frame and the image data of the third latest frame.

8. The ultrasound diagnostic device according to claim 6, wherein the control unit determines whether or not two pixels adjacent to each other in the azimuth direction in the image data of the second latest frame, the two pixels serving as determination subject pixels, satisfy a predetermined correlation condition, and when the correlation condition is satisfied as a result of the determination, the control unit sets pixel data of a pixel to be arranged between two pixels in the synthetic image, the two pixels corresponding to the determination subject pixels, to pixel data created based on pixel data related to the determination subject pixels.

9. The ultrasound diagnostic device according to claim 2, wherein the control unit sets the pixel data of the pixel in the synthetic image data, the pixel data corresponding to the changed portion, to the same pixel data as the pixel data in the image data of the second latest frame, the pixel data in the image data of the second latest frame corresponding to a pixel adjacent in an azimuth direction to either side of the changed portion where the pixel changed between the image data of the latest frame and the image data of the third latest frame.

10. The ultrasound diagnostic device according to claim 9, wherein the control unit sets pixel data of a pixel in the synthetic image data, the pixel data corresponding to a portion where a pixel did not change between the image data of the latest frame and the image data of the third latest frame, to pixel data of a pixel in the image data of the latest frame, the pixel data corresponding to the portion where the pixel did not change between the image data of the latest frame and the image data of the third latest frame.

11. The ultrasound diagnostic device according to claim 9, wherein the control unit determines whether or not two pixels adjacent to each other in the azimuth direction in the image data of the second latest frame, the two pixels serving as determination subject pixels, satisfy a predetermined correlation condition, and when the correlation condition is satisfied as a result of the determination, the control unit sets pixel data of a pixel to be arranged between two pixels in the synthetic image, the two pixels corresponding to the determination subject pixels, to pixel data created based on pixel data related to the determination subject pixels.

12. A nontransitory computer-readable medium having stored thereon a program that is executable by a computer, the computer being provided in an ultrasound diagnostic device including an ultrasound probe which includes n pieces of transducers being arranged in parallel, n satisfying $n>1$, the transducers outputting transmitted ultrasound waves toward a test body by a drive signal, and outputting received signals by receiving reflected ultrasound waves from the test body, the program being executable by the computer to execute functions comprising:
  a transmission function to supply the drive signal to selected transducers from among the n pieces of transducers;
  a reception function to receive received signals to be outputted from the selected transducers;
  a control function to sequentially select the transducers to be supplied with the drive signal from among the n pieces of transducers, wherein the control function shifts the transducers to be selected by a predetermined number in an array direction every time when each of the transmitted ultrasound waves is outputted; and
  an image processing function to create image data of an inside of the test body for each frame of a plurality of frames based on the received signals sequentially received by the receiver unit,
  wherein the control function switches a number of the transducers which are sequentially selected to be supplied with the drive signal for consecutive frames, by executing sequential selection of m pieces of the transducers arranged consecutively for a first frame and executing sequential selection of m+1 pieces of the transducers arranged consecutively for a second frame which is consecutive to the first frame, m satisfying $m<n$, and
  wherein every time when the image data of each frame is created, the image processing function creates synthetic image data obtained by synthesizing image data of at least two consecutive frames with each other.

* * * * *